(12) United States Patent
Benson et al.

(10) Patent No.: US 7,816,114 B2
(45) Date of Patent: Oct. 19, 2010

(54) METHODS OF USING CRYSTALS OF BETA AMYLOID CLEAVING ENZYME (BACE)

(75) Inventors: Timothy Benson, Kalamazoo, MI (US); D. Danielle Woods, Kalamazoo, MI (US); Donald Prince, Parchment, MI (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 12/329,558

(22) Filed: Dec. 6, 2008

(65) Prior Publication Data

US 2009/0170128 A1    Jul. 2, 2009

Related U.S. Application Data

(62) Division of application No. 10/143,723, filed on May 10, 2002, now Pat. No. 7,524,668.

(60) Provisional application No. 60/290,120, filed on May 10, 2001, provisional application No. 60/334,648, filed on Nov. 30, 2001.

(51) Int. Cl.
*C12N 9/50* (2006.01)
*G01N 31/00* (2006.01)

(52) U.S. Cl. .......................... 435/219; 436/4

(58) Field of Classification Search .................. None
See application file for complete search history.

(56) References Cited

U.S. PATENT DOCUMENTS

| | | | |
|---|---|---|---|
| 5,744,346 | A | 4/1998 | Chrysler et al. |
| 5,942,400 | A | 8/1999 | Anderson et al. |
| 6,221,645 | B1 | 4/2001 | Chrysler et al. |
| 6,225,103 | B1 | 5/2001 | Keolsch et al. |
| 6,245,884 | B1 | 6/2001 | Hook |
| 6,258,386 | B1 | 7/2001 | Xia et al. |
| 6,268,158 | B1 | 7/2001 | Pantoliano et al. |
| 6,291,223 | B1 | 9/2001 | Christie et al. |
| 6,297,021 | B1 | 10/2001 | Nienaber et al. |
| 6,329,163 | B1 | 12/2001 | Anderson et al. |
| 6,420,534 | B1 | 7/2002 | Gurney et al. |
| 6,440,698 | B1 | 8/2002 | Gurney et al. |
| 6,545,127 | B1 | 4/2003 | Tang et al. |
| 6,627,739 | B1 | 9/2003 | Anderson et al. |
| 7,217,556 | B1 | 5/2007 | Benson et al. |
| 7,384,773 | B1 | 6/2008 | Benson et al. |
| 7,442,537 | B1 | 10/2008 | Benson et al. |
| 7,524,668 | B1 | 4/2009 | Benson et al. |
| 7,601,528 | B1 | 10/2009 | Benson et al. |
| 2001/0018208 | A1 | 8/2001 | Gurney et al. |
| 2001/0021391 | A1 | 9/2001 | Gurney et al. |
| 2002/0037315 | A1 | 3/2002 | Gurney et al. |
| 2002/0049303 | A1 | 4/2002 | Tang et al. |
| 2002/0055459 | A1 | 5/2002 | Chopra et al. |
| 2002/0064819 | A1 | 5/2002 | Gurney et al. |
| 2002/0081634 | A1 | 6/2002 | Gurney et al. |
| 2002/0115600 | A1 | 8/2002 | Keolsch et al. |
| 2003/0095958 | A1 | 5/2003 | Bhisetti et al. |
| 2004/0014194 | A1 | 1/2004 | Beyer et al. |
| 2006/0136141 | A1 | 6/2006 | Benson et al. |
| 2008/0201123 | A1 | 8/2008 | Cosgrove |
| 2008/0215249 | A1 | 9/2008 | Benson et al. |
| 2009/0125259 | A1 | 5/2009 | Nicholls et al. |

FOREIGN PATENT DOCUMENTS

| | | |
|---|---|---|
| WO | WO 00/17369 | 3/2000 |
| WO | WO 01/00663 | 1/2001 |
| WO | WO 01/00665 | 1/2001 |
| WO | WO 01/49097 | 7/2001 |
| WO | WO 01/49098 | 7/2001 |
| WO | WO 01/50829 | 7/2001 |
| WO | WO 02/25276 | 3/2002 |
| WO | WO 01/23533 | 4/2002 |
| WO | WO 02/053594 | 7/2002 |
| WO | WO 03/012089 | 2/2003 |

OTHER PUBLICATIONS

McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Alvares et al., "Rat urate oxidase produced by recombinant baculovirus expression: formation of peroxisome crystalloid core-like structures", Jun. 1992 Proceedings of the National Academy of Sciences USA vol. 89: pp. 4908-4912.
Dealwis et al., "X-ray analysis at 2.0 Angstrom resolution of mouse submaxillary rennin complexed with a decapeptide inhibitor CH-66, based on the 4- 16 fragment of rat angiotensinogen", Feb. 1994, Journal of Molecular Biology, vol. 236: pp. 342-360.

(Continued)

*Primary Examiner*—Suzanne M. Noakes
(74) *Attorney, Agent, or Firm*—McDonnell Boehnen Hulbert & Berghoff LLP

(57) ABSTRACT

Methods of using monoclinic crystals of human beta-secretase (BACE) having unit cell dimensions of a, b, and c, wherein a is about 81±20 Å to about 101 Å, b is 103±20 Å, c is 100±20 Å, and α=γ=90°, and β is 105°±10° for crystals of symmetry P2$_1$ and a=73.1, b=105.1, c=50.5 Å and β is 94.8° for crystals of C2 symmetry in drug screening assays comprising selecting a potential modifier by adding the potential modifiers to an aqueous mixture of the crystal and detecting a measure of binding, such that the potential modifier that binds is selected as a potential drug.

15 Claims, 10 Drawing Sheets

OTHER PUBLICATIONS

Giege et al., Crystallogenesis of Biological Macromoleules: Facts and Perspectives, Jul. 1994m /acta /crystallographica Section D., vol. 50:pp. 339-350.

Kervinen et al., "Toward a universal inhibitor of retroviral proteases: Comparative analysis of the interactions of LP-130 complexed with proteases from HIV-1, FIV and EIAV", Nov. 1998, Protein Science, Bol. 7: pp. 2314-2323.

Bartlett et al., "CAVEAT: A program to facilitate the structure-derived design of biologically active molecules," Molecular Recognition: Chemical and Biological Problems, Royal Society of Chemistry, Special Pub No. 78:182-196 (1989).

Benson et al., "An enzyme-substrate complex involved in bacterial cell wall biosynthesis, " National Struct. Biolo. 1995 (8):644-53.

Berman et al., "The Protein Data Bank," Nucleic Acids Res. Jan. 1, 2000:28(1): 235-42.

Blundell et al., Protein Crystallography, Academic Press, New York, NY; title page, publication page, and table of contents only, 8 pages (1976).

Bohm, "The computer program LUDI: a new method for the de novo design of enzyme inhibitors," J Comput Aided Mol Des. 1992:6(1):61-78.

Branden et al., "Introduction to protein structure," Garland Publishing, Inc. , New York, NY 1999; Cover page, copyright page, and pp. 373-374.

Bruinzeel et al., "Recombinant insect cell expression and purification of human •-secretase (BACE-1) for X-ray crystallography," Protein Expr. Pruif. Oct. 2002: 26(1):139-148.

Ehehalt et al., "Splice variants of the •-site APP-cleaving enzyme BACE1 in human brain and pancreas," Biochem Biophys Res Commun. Apr. 26, 2002:293(1):30-37.

Farzan et al., "BACE2, a •-secretase homolog, cleaves at the • site and within the amyloid-• region of the amyloid-• precursor protein," Proc Natl Acad Sci USA Aug. 15, 2000:97(17):9712-9717.

Ghosh et al., "Structure-based design: Potent inhibitors of human brain memapsin 2 (•-secretase)," J Med Chem Aug 30, 2001:44(18):2865-2868.

Drenth, "Principles of Protein X-ray Crystallograph," Second Edition, 1994 Springer-Verlag New York, Inc. pp. 1-18.

Brunger, "X-PLOR: Version 3.1, a System for X-Ray Crystallography and NMR", Yale University Press, New Haven & London, 1992; cover page, publication page and table of contents; 13 pages.

Brunger et al., "Slow-cooling protocols for crystallographic refinement by simulated annealing," Acta Crystallogr A. Jul 1, 1990:46(Pt 7): 585-93.

Collaborative Computational Project, No. 4, "The CCP4 suite: programs for protein crystallography" Acta Cryst. 1994:D50:760-3.

CNX: Crystallograph and NMR eXplorer datasheet, Accelrys Corporate Headquarters, San Diego, CA (2001). [retrieved Aug. 30, 2002 from the Internet: URL:http://www.accelrys.com 2 pages.].

Eisen et al., "HOOK:A program for finding novel molecular architectures that satisfy the chemical and steric requirements of a macromolecule binding site," Proteins. 1994;19(3):199-221.

Epps et al., "The ligand affinity of proteins measured by isothermal denaturation kinetics," Anal Biochem. May 1, 2001;292(1):40-50.

Ermolieff et al., "Proteolytic activation of recombinant pro-memasin 2 (pro-beta-secretase) studied with new fluorogenic substrates," Biochemistry Oct 10, 2000;39(40):12450-6.

Fairlie et al., "Conformational selection of inhibitors and substrates by proteolytic enzymes: implications for drug design and polypeptide processing," J Med Chem. Apr. 6, 2000;43(7):1271-81.

Finzel, "LORE: Exploiting database of known structures," Meth. Enzymol. 1997;277(B):230-42.

Gillet et al., "SPROUT: a program for structure generation," J Comput Aided Mol Des. 1993(2):127-53.

Goodford, "A computational procedure for determining energetically favorable binding sites on biologically important macromolecules," J Med Chem Jul. 1985:28(7):849-57.

Goodsell et al., "Automated docking of substrates to proteins by simulated annealing," Proteins 1990;8(3)195-202.

Haniu et al., "Characterization of Alzheimer's beta -secretase protein BACE. A pepsin family member with unusual properties," J Biol Chem. Jul. 14, 2000;275(28):21099-106.

Hendrickson et al., "Selenomethiony proteins produced for analysis by multiwavelength anomalous diffraction (MAD): a vehicle for direct determination of three-dimensional structure," EMBO J. 1990;9(5):1665-72.

Hong et al., "Structure of the protease domain of memapsin 2 (beta-secretase) complexed with inhibitor," Science. Oct. 2000 6L 290(5489)L150-3.

Huang et al,. "A 3D-structural model of memapsin 2 protease generated from theoretical study," Acta Pharmacol Sin. Jan. 2001:22(1):50-56.

Hussain et al., "Identification of novel aspartic protease (Asp 2) as •-secretase," Mol Cell Neurosci. Dec. 1999;14(6):419-27.

Jiang et al, "Protein hydration observed by X-ray diffraction. Solvation properties of penicillopepsin and neuraminidase crystal structures," J Mol Biol. Oct. 14, 1994:243(1)100-15.

Kang et al., "The precursor of Alzheimer's disease amyloid a4 protein resembles a cell-surface receptor," Nature. Feb. 19, 1987;325(6106):733-6.

Kitaguchi et al., "Novel precursor of Alzheimer's disease amyloid protein shows protease inhibitory activity," Nature Feb 11, 1988;331(6156):530-2.

Kuntz et al., "A geometric approach to macromolecule-ligand interactions," J Mol Biol. Oct. 25, 1982:161(2):269-88.

Lattman, "Use of the Rotation and Translation Functions," Meth. Enzymol. 1985;115:55-77.

Lauri et al., CAVVEAT: a program to facilitate the design of organic molecules, J. Comput. Aided Mol. Des 1994;8:51-66.

Lin et al., Human aspartic protease memapsin 2 cleaves the •-secretase site of •-amyloid precursor protein, Proc Natl Acad Sci USA Feb. 15, 2000;97(4):1456-60.

Mallender et al., "Characterization of recombinant, soluble beta-secretase from an insect cell expression system," Mol Pharmacol Mar. 2001, 59(3):619-26.

Martin, "3D Database Searching in Drug Design," J. Med Chem 1992;35:2145-2154.

Meng et al., "Automated Docking with Grid-Based Energy Evaluation," J. Comp. Chem. 1992;13:505-524.

Miranker et al., "Functionality Maps of Binding Sites: A multiple Copy Simultaneous Search Method," Proteins: Struct. Funct. Gen. 1991;11:29-34.

National Institutes of Health, "BLAST 2 Sequences,"[online} United States; retrieved Aug. 29, 2001 from the Internet: <URL:http://www.ncbi.nlm.nih.gov/gorf/bl2.html.> 1 pg.

Navaza, "AMoRe: an automated package for molecular replacement," Acta Cryst. 1994; A50:157-163.

Nishibata et al., "Automatic Creation of Drug Candidate Structures Based on Receptor Structure. Starting Point for Artificial Lead Generation," Tetrahedron. 1991;47:8985-90.

Noren et al., "A general method for site-specific incorporation of unnatural amino acids into protein," Science Apr. 14, 1989;244(4901):182-8.

Otwinowski, "Maximum Likelihood Refinement of Heavy Atom Parameters," Isomorphous Replacement and Anomalous Scattering, Wolf et al., eds., Science & Engineering Research Council, Daresbury Laboratory, Warrington, U>K., Proceedings of the CCP4 Study Weekend, Jan. 25-26, 1991; pp. 80-86.

Park et al., "Molecular Characterization of Candidate •-secretases, BACE1 and BACE2." ScholarOne, Inc. [online] Session No. 180.11; Society for Neuroscience's 30th Annual Meeting, New Orleans, LA, Nov. 4-9, 2001 [retrieved on Oct. 29, 2001]. Retrieved from the Internet URL:<hhtpL//sfn.scholarone.com/itin2000/main.html?new_page_id=76&abstract)id=19280&is_tech=0 >, 1 page abstract.

Ponte et al., "A new A4 amyloid mRNA contains a domain homologous to serine proteinase inhibitors," Nature Feb. 11, 1988;331(6156):525-7.

Research Collaboratory for Structural Bioinformatics, "Protein Data Bank," [online] United States; retrieved Apr. 9, 2001 from the Internet: <URL:http:..www.rcsb.org/pdb/> 2 pages.

Research Collaboratory for Structural Bioinformatics, "Protein Data Bank," [online] United States; retrieved Aug. 30, 2002 from the Internet: <URL:http:..www.rcsb.org/pdb/> 8 pages.

Rossman, ed., The Molecular Replacement Method—A Collection of Papers on the Use of Non-Crystallographic Symmetry, Intl. Sci. Rev. Ser. No. 13, Gordon & Breach, New York, NY; title page, publication page, and table of contents only, 6 pages (1972).

Sack, "CHAIN-A Crystallographic Modeling Program," J. Mol. Graph 1988;6:224-25.

Sauder et al., "Modeling of substrate specificity of the Alzheimer's disease amyloid precursor protein beta-secretase," J. Mol Biol Jul. 7, 2000;300(2):241-8.

Shi et al., "The pro domain of •-secretase does not confer strict zymogen-like properties but does assist proper folding of the protease domain," J Biol Chem. Mar. 30, 2001;276(13):10366-73.

Skovronsky et al., "Beta-secretase revealed : starting gate for race to novel therapies for Alzheimer's disease," Trends Pharmacol Sci. May 2000;21(5):161-3.

Tanzi et al., "Protease inhibitor domain encoded by an amyloid protein precursor mRNA associated with Alzheimer's disease," Nature. Feb. 11, 1988; 331(6156): 528.30.

Tatusova et al., "BLAST 2 Sequences, a new tool for comparing protein and nucleotide sequences," FEMS Microbiol Lett. 1999;174:247-50 (program available at http://www.ncbinlm.nih.gov/gorf/bl2.html).

Travis, "Proteins and organic solvents make an eye-opening mix," Science. 1993 No. 26;262(5138:1374.

Turner et al., "Substrate specificity of memapsin 2 (beta-secretase): Basis for inhibitor drug design for Alzheimer's disease," Experimental Biology 2001 Conference. Orlando, Florida, USA. Mar. 31-Apr. 4, 2001. Abstracts, part I. FASEB J. 2001 Nar 7;15(6):A538.

Van Duyne et al., "Atomic Structures of the Human Immunophilin FKBP-12 Complexes with FK506 and Rapamycin," J. Mol. Biol. 1993;229:105-24.

Vassar et al., "•-secretase cleavage of Alzheimer's amyloid precursor protein by the transmembrane aspartic protease BACE," Science. Oct. 22, 1999;286(5440):735-41.

Wyckoff et al., eds., Methods in Enzymology, vol. 114, Diffraction Methods for Biological Macromolecules, Academic Press, Orlando, FL, title page, publication page, and table of contents only, 5 pages total (1985).

Wyckoff et al., eds., Methods in Enzymology, vol. 115, Diffraction Methods for Biological Macromolecules, Academic Press, Orlando, FL; title page, publication page, and table of contents only, 4 pages (1985).

Yan et al., (1999), "membrane-anchored aspartyl protease with Alzheimer's disease •-secretase activity," Nature. Dec. 2, 1999;402(6761):533-7.

McPherson et al., "The science of macromolecular crystallization," Aug. 1995, Structure, vol. 3, pp. 759-768.

Tang et al., Structural evidence for gene duplication in the evolution of the acid proteases: Feb. 1978, Nature, vol. 271, pp. 618-621.

Van Der Klei et al., <<Biosynthesis and assembly of alcohol oxidase, a peroxisomal matrix protein in methlotrophic yeasts: a review, Apr. 1991, Yeast, vol. 7, pp. 195-209.

Kierzek et al., (2001) Biophys Chem 91:1-20.

Ducruix et al., "Crystallization of Nucleic Acids and Proteins, A Practical Approach", Oxford University Press, New York 1999, p. 394.

Wang et al., "Crystallization of Glycosylated Human BACE Protease Domain Expressed in Trichoplusia ni", Biochimica et Biophysica Acta, (2004), vol. 1698, pp. 255-259.

Waugh, "Making the Most of Affinity Tags", Trends in Biotechnology, (2005), vol. 23, No. 6, pp. 316-320.

Witkowski, et al., "Conversion of a β-Ketoacyl Synthase to a Malonyl Decarboyylase by Replacement of the Active-Site Cysteine with Glutamine", Biochemistry, (1999), vol. 38, pp. 11643-11650.

Timasheff, "Crystallization", Encyclopedia of Molecular Biology, vol. 1, (1999), John Wiley-Interscience Publication, p. 586.

Sinha et al., "Purification and cloning of amyloid precursor protein •-secretase from human brain," Nature. Dec. 2, 1999;402(6761)537-40.

Budisa et al., "High-level biosynthetic substitution of methionine in proteins by its analogs 2-aminohexanoic acid, selenomethionine, telluromethionine and ethionine in *Escherichia coli*," Eur. J. Biochem FEBS, 230:788-796 (1995).

Wiencek, J.M., "New Strategies for Protein Crystal Growth," Annu. Rev. Biomed. Egn., 01:505-534 (1999).

Buts, Lieven et al., "Impact of natural variation in bacterial Fl7G adhesins on crystallization behaviour," Acta Cryst., D61, 1149-1159 (2005).

Skarzynski et al., "Industrial perspective on X-ray data collection and analysis," Acta Cryst., D62, 102-107 (2006).

Weber, Patricia C., "[2] Overview of Protein Crystrallization Methods," Methods in Enzymology, 276:13-22 (1997).

"Buffers," obtained at www.vanderbilt.edu/AnS/Chemistry/Rizzo/stuff/Buffers/buffers.html, last viewed on Mar. 12, 2008.

Nienaber et al., "Discovering novel ligands for macromolecules using X-ray crystallographic screening," Nature Biotechnology, 18:1105-1108 (2000).

Emmons et al., "Large-scale Purification of Human BACE Expressed in Mammalian Cells and Removal of the Prosegment with HIV-1 Protease to Improve Crystal Diffraction," Protein and Peptide Letter, 15:119-130 (2008).

Branden et al., "Prediction, Engineering, and Design of Protein Structures," Introduction to Protein Structure, Garland Publishing, Inc., p. 247 (1991).

* cited by examiner

Figure 10

```
SEQ ID No:1   BACE_ecoli_pet11a   MASMTGGQQMGRGSMAGVLPAHGTQHGIRLPLRSGLGGAPLGLRLPRETD
SEQ ID No:2   BACE_ecoli_pQE80L   -------MRGSHHHHHHGSIETDTQHGIRLPLRSGLGGAPLGLRLPRETD
SEQ ID No:3   BACE_ecoli_pQE70    --------------------------------------------------

BACE_ecoli_pet11a   EEPEEPGRRGSFVEMVDNLRGKSGQGYYVEMTVGSPPQTLNILVDTGSSN
              BACE_ecoli_pQE80L   EEPEEPGRRGSFVEMVDNLRGKSGQGYYVEMTVGSPPQTLNILVDTGSSN
              BACE_ecoli_pQE70    -------MRGSFVEMVDNLRGKSGQGYYVEMTVGSPPQTLNILVDTGSSN
                                  First residue visible (residue 61P)↑  ↑Residue 1

BACE_ecoli_pet11a   FAVGAAPHPFLHRYYQRQLSSTYRDLRKGVYVPYTQGKWEGELGTDLVSI
              BACE_ecoli_pQE80L   FAVGAAPHPFLHRYYQRQLSSTYRDLRKGVYVPYTQGKWEGELGTDLVSI
              BACE_ecoli_pQE70    FAVGAAPHPFLHRYYQRQLSSTYRDLRKGVYVPYTQGKWEGELGTDLVSI BACE_ecoli_pet11a   PHGPNVTVRANIAAITESDKFFINGSNWEGILGLAYAEIARPDDSLEPFF
              BACE_ecoli_pQE80L   PHGPNVTVRANIAAITESDKFFINGSNWEGILGLAYAEIARPDDSLEPFF
              BACE_ecoli_pQE70    PHGPNVTVRANIAAITESDKFFINGSNWEGILGLAYAEIARPDDSLEPFF BACE_ecoli_pet11a   DSLVKQTHVPNLFSLQLCGAGFPLNQSEVLASVGGSMIIGGIDHSLYTGS
              BACE_ecoli_pQE80L   DSLVKQTHVPNLFSLQLCGAGFPLNQSEVLASVGGSMIIGGIDHSLYTGS
              BACE_ecoli_pQE70    DSLVKQTHVPNLFSLQLCGAGFPLNQSEVLASVGGSMIIGGIDHSLYTGS BACE_ecoli_pet11a   LWYTPIRREWYYEVIIVRVEINGQDLKMDCKEYNYDKSIVDSGTTNLRLP
              BACE_ecoli_pQE80L   LWYTPIRREWYYEVIIVRVEINGQDLKMDCKEYNYDKSIVDSGTTNLRLP
              BACE_ecoli_pQE70    LWYTPIRREWYYEVIIVRVEINGQDLKMDCKEYNYDKSIVDSGTTNLRLP BACE_ecoli_pet11a   KKVFEAAVKSIKAASSTEKFPDGFWLGEQLVCWQAGTTPWNIFPVISLYL
              BACE_ecoli_pQE80L   KKVFEAAVKSIKAASSTEKFPDGFWLGEQLVCWQAGTTPWNIFPVISLYL
              BACE_ecoli_pQE70    KKVFEAAVKSIKAASSTEKFPDGFWLGEQLVCWQAGTTPWNIFPVISLYL BACE_ecoli_pet11a   MGEVTNQSFRITILPQQYLRPVEDVATSQDDCYKFAISQSSTGTVMGAVI
              BACE_ecoli_pQE80L   MGEVTNQSFRITILPQQYLRPVEDVATSQDDCYKFAISQSSTGTVMGAVI
              BACE_ecoli_pQE70    MGEVTNQSFRITILPQQYLRPVEDVATSQDDCYKFAISQSSTGTVMGAVI BACE_ecoli_pet11a   MEGFYVVFDRARKRIGFAVSACHVHDEFRTAAVEGPFVTLDMEDCGYNIP
              BACE_ecoli_pQE80L   MEGFYVVFDRARKRIGFAVSACHVHDEFRTAAVEGPFVTLDMEDCGYNIP
              BACE_ecoli_pQE70    MEGFYVVFDRARKRIGFAVSACHVHDEFRTAAVEGPFVTLDMEDCGYNIP BACE_ecoli_pet11a   QTDES---------
              BACE_ecoli_pQE80L   QTDES---------
              BACE_ecoli_pQE70    QTDESRSHHHHHH
```

Figure 11

SEQ ID NO: 1 bace_ecoli
SEQ ID NO: 5 bace_cho_hiv

Signal peptide

```
bace_ecoli     MASMTGGQQMGRGSMAGVLPAHGTQHGIRLPLRSGLGGAPLGLRLPRETD
bace_cho_hiv   --------------------------------------------------
```

HIV Protease Cleavage Site (F $^{39}$-V$^{40}$)

```
bace_ecoli     EEPEEPGRRGSFVEMVDNLRGKSGQGYYVEMTVGSPPQTLNILVDTGSSN
bace_cho_hiv   -----------VEMVDNLRGKSGQGYYVEMTVGSPPQTLNILVDTGSSN
```

First residue in X-ray structure (residue #1)

```
bace_ecoli     FAVGAAPHPFLHRYYQRQLSSTYRDLRKGVYVPYTQGKWEGELGTDLVSI
bace_cho_hiv   FAVGAAPHPFLHRYYQRQLSSTYRDLRKGVYVPYTQGKWEGELGTDLVSI bace_ecoli     PHGPNVTVRANIAAITESDKFFINGSNWEGILGLAYAEIARPDDSLEPFF
bace_cho_hiv   PHGPNVTVRANIAAITESDKFFINGSNWEGILGLAYAEIARPDDSLEPFF bace_ecoli     DSLVKQTHVPNLFSLQLCGAGFPLNQSEVLASVGGSMIIGGIDHSLYTGS
bace_cho_hiv   DSLVKQTHVPNLFSLQLCGAGFPLNQSEVLASVGGSMIIGGIDHSLYTGS bace_ecoli     LWYTPIRREWYYEVIIVRVEINGQDLKMDCKEYNYDKSIVDSGTTNLRLP
bace_cho_hiv   LWYTPIRREWYYEVIIVRVEINGQDLKMDCKEYNYDKSIVDSGTTNLRLP bace_ecoli     KKVFEAAVKSIKAASSTEKFPDGFWLGEQLVCWQAGTTPWNIFPVISLYL
bace_cho_hiv   KKVFEAAVKSIKAASSTEKFPDGFWLGEQLVCWQAGTTPWNIFPVISLYL bace_ecoli     MGEVTNQSFRITILPQQYLRPVEDVATSQDDCYKFAISQSSTGTVMGAVI
bace_cho_hiv   MGEVTNQSFRITILPQQYLRPVEDVATSQDDCYKFAISQSSTGTVMGAVI bace_ecoli     MEGFYVVFDRARKRIGFAVSACHVHDEFRTAAVEGPFVTLDMEDCGYNIP
bace_cho_hiv   MEGFYVVFDRARKRIGFAVSACHVHDEFRTAAVEGPFVTLDMEDCGYNIP bace_ecoli     QTDES
bace_cho_hiv   QTDESHHHHHH
``` under
US 7,816,114 B2

METHODS OF USING CRYSTALS OF BETA AMYLOID CLEAVING ENZYME (BACE)

RELATED APPLICATIONS

This application is a divisional application and claims the benefit of U.S. application Ser. No. 10/143,723, filed May 10, 2002, now U.S. Pat. No. 7,524,668, which claims the benefit of the U.S. Provisional Application Ser. No. 60/290,120, filed May 10, 2001, and 60/334,648, filed Nov. 30, 2001, both of which are incorporated herein by reference in their entireties.

This application incorporates by reference the material contained on the duplicate (2) compact discs submitted herewith. Each disc contains the following files.

| Name | Size | Contents | Date of File Creation |
| --- | --- | --- | --- |
| table_1.txt | 735 kbytes | Table 1 | Nov. 15, 2001 |
| table_2.txt | 273 kbytes | Table 2 | Nov. 15, 2001 |
| table_3.txt | 470 kbytes | Table 3 | May 9, 2001 |

FIELD OF THE INVENTION

This invention relates to the crystallization and structure determination of BACE, also known as memapsin 2 and beta secretase, from human (*Homo sapiens*), particularly in a form as produced in an *E. coli* expression system.

BACKGROUND

Alzheimer's disease (AD) causes progressive dementia with consequent formation of amyloid plaques, neurofibrillary tangles, gliosis and neuronal loss. The disease occurs in both genetic and sporadic forms whose clinical course and pathological features are quite similar. Three genes have been discovered to date which, when mutated, cause an autosomal dominant form of Alzheimer's disease. These encode the amyloid protein precursor (APP) and two related proteins, presenilin-1 (PS1) and presenilin-2 (PS2), which, as their names suggest, are structurally and functionally related. Mutations in any of the three proteins have been observed to enhance proteolytic processing of APP via an intracellular pathway that produces amyloid beta peptide. (Aβ peptide, or sometimes here as Abeta), a 40-42 amino acid long peptide that is the primary component of amyloid plaque in AD.

Dysregulation of intracellular pathways for proteolytic processing may be central to the pathophysiology of AD. In the case of plaque formation, mutations in APP, PS1 or PS2 consistently alter the proteolytic processing of APP so as to enhance formation of Aβ 1-42, a form of the Aβ peptide which seems to be particularly amyloidogenic, and thus very important in AD. Different forms of APP range in size from 695-770 amino acids, localize to the cell surface, and have a single C-terminal transmembrane domain. The Abeta peptide is derived from a region of APP adjacent to and containing a portion of the transmembrane domain. Normally, processing of APP at the α-secretase site cleaves the midregion of the Aβ sequence adjacent to the membrane and releases the soluble, extracellular domain of APP from the cell surface. This α-secretase APP processing creates soluble APP-α, which is normal and not thought to contribute to AD. Pathological processing of APP at the β- and γ-secretase sites, which are located N-terminal and C-terminal to the α-secretase site, respectively, produces a very different result than processing at the α site. Sequential processing at the β- and γ-secretase sites releases the Aβ peptide, a peptide possibly very important in AD pathogenesis. Processing at the β- and γ-secretase sites can occur in both the endoplasmic reticulum (in neurons) and in the endosomal/lysosomal pathway after reinternalization of cell surface APP (in all cells). Despite intense efforts, for 10 years or more, to identify the enzymes responsible for processing APP at the β and γ sites, to produce the Aβ peptide, those proteases remained unknown until recently. The identification and characterization of the β secretase enzyme, termed Aspartyl Protease 2 (Asp2) or BACE has been established. Since the β-secretase catalyzes the committed step in formation of the Aβ peptide, it has become a key target in the search for therapeutic agents to combat Alzheimer's disease. It is believed that inhibition of BACE should slow or stop the onset of amyloid plaque formation and the associated symptoms of Alzheimer's disease.

In addition, the X-ray crystal structure of human BACE in complex with a peptide inhibitor was solved and published (Hong et al., *Science* 290:150-53 (2000)) from protein expressed in *E. coli* that contained no covalent sugar (glycosylation) at any of the four putative glycosylation sites within the enzyme.

SUMMARY OF THE INVENTION

In one aspect, the present invention provides a crystal of BACE including a unit cell defined by the dimensions a, b, c, α, β, and γ, wherein a is about 61 Å to about 101 Å, b is about 83 Å to about 123 Å, c is about 80 Å to about 120 Å, α=γ=90°, and β is about 95° to about 115°. Preferably, the crystal has monoclinic space group symmetry $P2_1$.

In another aspect, the present invention provides a crystal of BACE having monoclinic space group symmetry C2.

In another aspect, the present invention provides a crystal of BACE including a unit cell having dimensions of a, b, and c, wherein a is about 53 Å to about 103 Å, b is about 85 Å to about 125 Å, and c is about 40 Å to about 60 Å; and α=γ=90°, and β is about 85° to about 105°. Preferably, the crystal has monoclinic space group symmetry C2.

The present invention also provides methods of using the crystals of BACE in a drug screening assay.

In another aspect, the present invention provides a method for crystallizing a human BACE molecule or molecular complex. In one embodiment, the method includes preparing purified human BACE in the presence of a potential modifier, and crystallizing the human BACE from a solution including the purified BACE and the potential modifier, wherein the solution has a pH of about 4.5 to about 5.6. In another embodiment, the method includes preparing purified human BACE in the presence of a potential modifier, and adding a precipitant salt to a solution including the purified BACE and the potential modifier.

In another aspect, the present invention provides a molecule or molecular complex that that forms a crystal having a unit cell defined by the dimensions a, b, c, α, β, and γ, wherein a is about 61 Å to about 101 Å, b is about 83 Å to about 123 Å, c is about 80 Å to about 120 Å, α=γ=90°, and β is about 95° to about 115°, and that includes at least a portion of a human BACE or BACE-like binding pocket, wherein the binding pocket includes the amino acids listed in Table 4A, the binding pocket being defined by a set of points having a root mean square deviation of less than about 0.65 Å from points representing the backbone atoms of said amino acids as represented by the structure coordinates listed in Table 1.

In another aspect, the present invention provides a molecule or molecular complex that forms a crystal having monoclinic space group symmetry C2, and that includes at least a portion of a human BACE binding pocket, wherein the binding pocket includes the amino acids listed in Table 4B, the binding pocket being defined by a set of points having a root mean square deviation of less than about 0.65 Å from points representing the backbone atoms of said amino acids as represented by the structure coordinates listed in Table 2.

In another aspect, the present invention provides a scalable three-dimensional configuration of points, at least a portion of said points being derived from structure coordinates of at least a portion of a human BACE molecule or molecular complex listed in Table 1 including a human BACE or BACE-like binding pocket, wherein the human BACE molecule or molecular complex forms a crystal having a unit cell defined by the dimensions a, b, c, α, β, and γ, wherein a is about 61 Å to about 101 Å, b is about 83 Å to about 123 Å, c is about 80 Å to about 120 Å, α=γ=90°, and β is about 95° to about 115°. Preferably, the scalable three-dimensional configuration of points is displayed as a holographic image, a stereodiagram, a model, or a computer-displayed image.

In another aspect, the present invention provides a scalable three-dimensional configuration of points, at least a portion of said points being derived from structure coordinates of at least a portion of a human BACE molecule or molecular complex listed in Table 2 including a human BACE or BACE-like binding pocket, wherein the human BACE molecule or molecular complex forms a crystal having monoclinic space group symmetry C2.

In another aspect, the present invention provides a machine-readable data storage medium including a data storage material encoded with machine readable data which, when using a machine programmed with instructions for using said data, displays a graphical three-dimensional representation of a molecule or molecular complex. In one embodiment the molecule or molecular complex includes at least a portion of a human BACE or BACE-like binding pocket including the amino acids listed in Table 4A, the binding pocket defined by a set of points having a root mean square deviation of less than about 0.65 Å from points representing the backbone atoms of said amino acids as represented by structure coordinates listed in Table 1 of a human BACE or BACE-like molecule or molecular complex that forms a crystal having a unit cell defined by the dimensions a, b, c, α, β, and γ, wherein a is about 61 Å to about 101 Å, b is about 83 Å about 123 Å, c is about 80 Å to about 120 Å, α=γ=90°, and β is about 95° to about 115°. In another embodiment, the molecule or molecular complex includes at least a portion of a human BACE or BACE-like binding pocket including the amino acids listed in Table 4B, the binding pocket defined by a set of points having a root mean square deviation of less than about 0.65 Å from points representing the backbone atoms of said amino acids as represented by structure coordinates listed in Table 2 of a human BACE or BACE-like molecule or molecular complex that forms a crystal having monoclinic space group symmetry C2.

In another aspect, the present invention provides a method for obtaining structural information about a molecule or a molecular complex of unknown structure. In one embodiment, the method includes crystallizing the molecule or molecular complex; generating an x-ray diffraction pattern from the crystallized molecule or molecular complex; and applying to the x-ray diffraction pattern at least a portion of the structure coordinates as set forth in Table 1 for human BACE that forms a crystal having a unit cell defined by the dimensions a, b, c, α, β, and γ, wherein a is about 61 Å to about 101 Å, b is about 83 Å to about 123 Å, c is about 80 Å to about 120 Å, α=γ=90°, and β is about 95° to about 115°, to generate a three-dimensional electron density map of at least a portion of the molecule or molecular complex whose structure is unknown. In another embodiment, the method includes crystallizing the molecule or molecular complex; generating an x-ray diffraction pattern from the crystallized molecule or molecular complex; and applying at least a portion of the structure coordinates for human BACE set forth in Table 2 for human BACE that forms a crystal having monoclinic space group symmetry C2 to the x-ray diffraction pattern to generate a three-dimensional electron density map of at least a portion of the molecule or molecular complex whose structure is unknown.

In another aspect, the present invention provides a method for homology modeling a human BACE homolog. In one embodiment, the method includes aligning the amino acid sequence of a human BACE homolog with an amino acid sequence of human BACE and incorporating the sequence of the human BACE homolog into a model of human BACE formed from structure coordinates as set forth in Table 1 for human BACE that forms a crystal having a unit cell defined by the dimensions a, b, c, α, β, and γ, wherein a is about 61 Å to about 101 Å, b is about 83 Å to about 123 Å, c is about 80 Å to about 120 Å, α=γ90°, and β is about 95° to about 115°, to yield a preliminary model of the human BACE homolog; subjecting the preliminary model to energy minimization to yield an energy minimized model; and remodeling regions of the energy minimized model where stereochemistry restraints are violated to yield a final model of the human BACE homolog. In another embodiment, the method includes aligning the amino acid sequence of a human BACE homolog with an amino acid sequence of human BACE and incorporating the sequence of the human BACE homolog into a model of human BACE derived from human BACE structure coordinates set forth in Table 2 for human BACE that forms a crystal having monoclinic space group symmetry C2 to yield a preliminary model of the human BACE homolog; subjecting the preliminary model to energy minimization to yield an energy minimized model; and remodeling regions of the energy minimized model where stereochemistry restraints are violated to yield a final model of the human BACE homolog.

In another aspect, the present invention provides computer-assisted methods for identifying, designing, or making a potential modifier of human beta secretase activity. Preferably the methods include screening a library of chemical entities.

ABBREVIATIONS

The following abbreviations may be used throughout this disclosure:
Alzheimer's disease (AD)
3-[(1,1-Dimethylhydroxyethyl)amino]-2-hydroxy-1-propanesulfonic acid (AMPSO)
Amyloid beta peptide (AO peptide or Abeta)
Amyloid protein precursor (APP)
Aspartyl protease 2 (Asp2)
Beta amyloid cleaving enzyme (BACE, memapsin 2, beta secretase)
β-Mercaptoethanol (BME)
3-Cyclohexylamino-1-propanesulfonic acid (CAPS)
Dimethyl sulfoxide (DMSO)
Ethylenediaminetetraacetic acid (EDTA)
4-(2-Hydroxyethyl)-1-piperazineethanesulfonic acid (HEPES)
2-Methyl-2,4-pentanediol (MPD)
4-Morpholineethanesulfonic acid (MES)
Multiple anomalous dispersion (MAD)

Presenilin-1 (PS1)
Presenilin-2 (PS2)
Poly(ethylene glycol) (PEG)
2-Amino-2-hydroxymethyl-1,3-propanediol (TRIS)
TE-TRIS-EDTA The following amino acid abbreviations are used throughout this disclosure:

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

BRIEF DESCRIPTION OF THE FIGURES

FIG. 10 depicts the sequences of the three E. coli constructs for recombinant human BACE (SEQ ID NO:1, SEQ ID NO:2, and SEQ ID NO:3) used to obtain the crystals described. The first visible residue in the crystal structures is indicated.

FIG. 11 depicts the sequence alignment of the E. coli expressed recombinant human beta sectetase (SEQ ID NO:1) and the CHO cell expressed recombinant human beta secretase proteolytically cleaved with HIV protease (SEQ ID NO:5) present in the crystal structure.

DETAILED DESCRIPTION OF THE PREFERRED EMBODIMENTS

Figure 1:
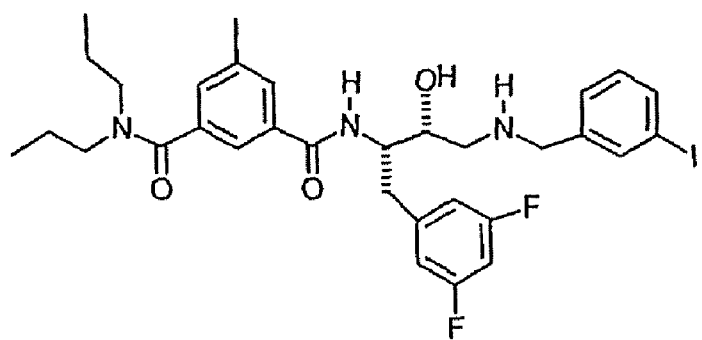
FIG. 1 is an illustration of the chemical structure of an inhibitor used in co-crystallization experiments.

Tables 1, 2, and 3 list atomic structure coordinates derived by x-ray diffraction of crystals having space groups $P2_1$, C2, and $P4_32_12$, respectively, of human BACE expressed in E. coli. Column 2 lists a number for the atom in the structure. Column 3 lists the element whose coordinates are measured. The first letter in the column defines the element. Column 4 lists the type of amino acid. Column 5 lists a number for the amino acid in the structure. Columns 6-8 list the crystallographic coordinates X, Y, and Z respectively. The crystallographic coordinates define the atomic position of the element measured. Column 9 lists an occupancy factor that refers to the fraction of the molecules in which each atom occupies the position specified by the coordinates. A value of "1" indicates that each atom has the same conformation, i.e., the same position, in all molecules of the crystal. Column 10 lists a thermal factor "B" that measures movement of the atom around its atomic center. Column 11 lists the chain id (AA for molecule A in the asymmetric unit, BB for molecule B in the asymmetric unit, CC for molecule C in the asymmetric unit, WW for water molecules, and LL for inhibitor molecules). Column 12 lists the element whose coordinates are measured.

Crystalline Form(s) and Method of Making

The three-dimensional structure of human BACE was solved using x-ray crystallography to 2.15 Å resolution for the $P2_1$ crystal form and 1.7 Å resolution for the C2 crystal form. Accordingly, the invention includes a human BACE crystal and/or a crystal with human BACE co-crystallized with a ligand. As used herein, "ligand" refers to a chemical entity that can form a reversible complex with the protein and that could function as a drug candidate (e.g., modifiers and inhibitors). Thus, the term "ligand" as used herein does not include chemical entities that could not function as a drug candidate (e.g., water, metal ions, and solvents). The crystal has monoclinic space group symmetry $P2_1$ or C2. The crystal includes monoclinic shaped unit cells, the $P2_1$ unit cell preferably having dimensions in which a=81±20 Å, b=103±20 Å, c=100±20 Å, α=γ=90°, β=105±10°, and the C2 unit cell preferably having dimensions in which a=73±20 Å, b=105±20 Å, c=50±10 Å, α=γ=90°, β=95±10°. The $P2_1$ crystal form is a monomer with three monomers in the asymmetric unit and the C2 crystal form is a monomer with a single monomer in the asymmetric unit.

According to the present invention, human BACE can be isolated from a variety of bacterial expression systems, for example, the E. coli strain BL21.

As used herein, a "molecular complex" means a protein in covalent or non-covalent association with a chemical entity (e.g., a ligand). In one embodiment, molecular complexes of purified human BACE at a concentration of about 1 mg/ml to about 80 mg/ml in a solution of about 100 mM sodium borate (e.g., pH 8.5) may be crystallized in the presence of a modifier at a concentration of about 0.001 to about 10 mM. Optionally, the solution includes about 0% by volume to about 40% by volume organic solvent (e.g., DMSO). Preferably, the solution is buffered to a pH of about 4.0 to about 6.5 and more preferably about 4.5 to about 5.6.

In another embodiment, molecular complexes of purified human BACE at a concentration of about 1 mg/ml to about 80 mg/ml in a solution of 100 mM sodium borate pH 8.5 may be crystallized in the presence of an inhibitor at a concentration from about 0.001 to about 10 mM, for example, from a solution including about 4% by weight/volume (w/v) to about 50% by w/v of PEG (e.g., PEG 3000) as the precipitant, and about 0% by volume to about 40% by volume organic solvent (such as DMSO), wherein the solution is buffered to a pH of about 4.0 to about 6.5 (preferably, a pH of about 4.5 to about 5.6). In addition, the percent weight/volume of the precipitant, e.g., PEG, may be greater than 30% when utilizing lower molecular weight PEG. For example, the crystallization procedure may include between about 4% weight/volume to about 40% weight/volume of PEG 750.

Optionally, the solution may include, for example, at most about 40% by weight ethylene glycol or glycerol. The solution may optionally include at most about 40% by weight of an organic solvent (e.g., dimethylsulfoxide or 2-methyl-2,4-pentanediol).

A buffer having a $pK_a$ of about 3 to about 7.5 is preferred for use in the crystallization method. A particularly preferred buffer is about 10 mM to about 200 mM ammonium citrate. Variation in buffer and buffer pH, phosphate salts as well as other additives such as PEG, PEG-MME, PEG-DME, or polyoxyalkylenepolyamines is apparent to those skilled in the art and may result in similar crystals.

Optionally, crystallization of the molecular complex may be induced by the addition of a precipitant salt to the solution. Precipitant salts for precipitating proteins are well known to those of skill in the art, and candidate precipitant salts can easily be screened for their ability to precipitate the desired protein. Precipitant salts include, for example, sodium hydrogenphosphate, sodium dihydrogenphosphate, potassium hydrogenphosphate, potassium dihydrogenphosphate, ammonium phosphate, ammonium sulfate, potassium phosphate, sodium citrate, sodium malonate, sodium acetate, sodium tartrate, ammonium formate, magnesium sulfate, and combinations thereof. A preferred precipitant salt includes, for example, ammonium phosphate. When precipitant salt is added to the solution, the solution preferably includes about 0.001 M to about 2.5 M salt.

The invention further includes a human BACE crystal that is isomorphous with a human BACE crystal having a unit cell defined by the dimensions a, b, c, $\alpha$, $\beta$, and $\gamma$, wherein a is about 61 Å to about 101 Å, b is about 83 Å to about 123 Å, c is about 80 Å to about 120 Å; $\alpha=\gamma=90°$, and $\beta$ is about 95° to about 115°; or wherein a is about 53 Å to about 93 Å, b is about 85 Å to about 125 Å, and c is about 40 Å to about 60 Å; and $\alpha=\gamma=90°$, and $\beta$ is about 85° to about 125°.

X-Ray Crystallographic Analysis

Each of the constituent amino acids of human BACE is defined by a set of structure coordinates as set forth in Table 1 or Table 2. The term "structure coordinates" refers to Cartesian coordinates derived from mathematical equations related to the patterns obtained on diffraction of a monochromatic beam of x-rays by the atoms (scattering centers) of a human BACE complex in crystal form. The diffraction data are used to calculate an electron density map of the repeating unit of the crystal. The electron density maps are then used to establish the positions of the individual atoms of the human BACE protein or protein/ligand complex.

Slight variations in structure coordinates can be generated by mathematically manipulating the human BACE or human BACE/ligand structure coordinates. For example, the structure coordinates set forth in Table 1 or Table 2 could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little effect on overall shape. If such variations are within an acceptable standard error as compared to the original coordinates, the resulting three-dimensional shape is considered to be structurally equivalent. Structural equivalence is described in more detail below.

It should be noted that slight variations in individual structure coordinates of the human BACE would not be expected to significantly alter the nature of chemical entities such as ligands that could associate with the binding pockets. In this context, the phrase "associating with" refers to a condition of proximity between a chemical entity, or portions thereof, and a human BACE molecule or portions thereof. The association may be non-covalent, wherein the juxtaposition is energetically favored by hydrogen bonding, van der Waals forces, or electrostatic interactions, or it may be covalent.

Thus, for example, a ligand that bound to a binding pocket of human BACE would also be expected to bind to or interfere with a structurally equivalent binding pocket.

For the purpose of this invention, any molecule or molecular complex or binding pocket thereof, or any portion thereof, that has a root mean square deviation of conserved residue backbone atoms (N, C$\alpha$, C, O) of less than about 0.65 Å, when superimposed on the relevant backbone atoms described by the reference structure coordinates listed in Table 1 and/or Table 2, is considered "structurally equivalent" to the reference molecule. That is to say, the crystal structures of those portions of the two molecules are substantially identical, within acceptable error. As used herein, "residue" refers to one or more atoms. Particularly preferred structurally equivalent molecules or molecular complexes are those that are defined by the entire set of structure coordinates listed in Table 1 or Table 2± a root mean square deviation from the conserved backbone atoms of those amino acids of less than about 0.65 Å. More preferably, the root mean square deviation is at most about 0.5 Å. Other embodiments of this invention include a molecular complex defined by the structure coordinates listed in Table 1 for those amino acids listed in Table 4A, Table 5A, or Table 6A, ± a root mean square deviation from the conserved backbone atoms of those amino acids of less than about 0.65 Å, preferably at most about 0.5 Å. Still another embodiment of this invention includes a molecular complex defined by the structure coordinates listed in Table 2 for those amino acids listed in Table 4B, Table 5B, or Table 6B, ± a root mean square deviation from the conserved backbone atoms of those amino acids of less than about 0.65 Å, preferably at most about 0.5 Å.

The term "root mean square deviation" means the square root of the arithmetic mean of the squares of the deviations. It is a way to express the deviation or variation from a trend or object. For purposes of this invention, the "root mean square deviation" defines the variation in the backbone of a protein from the backbone of human BACE or a binding pocket portion thereof, as defined by the structure coordinates of human BACE described herein.

It will be readily apparent to those of skill in the art that the numbering of amino acids in other isoforms of human BACE may be different than that of human BACE expressed in *E. coli*.

Active Site and Other Structural Features

Applicants' invention provides information about the shape and structure of the binding pocket of human BACE in the presence of a modifier. The secondary structure of the human BACE monomer includes two domains consistent with a typical aspartic protease fold.

Binding pockets are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or any parts of the binding pocket. An understanding of such associations helps lead to the design of drugs having more favorable associations with their target, and thus improved biological effects. Therefore, this information is valuable in designing potential modifiers of BACE-like binding pockets, as discussed in more detail below.

The term "binding pocket," as used herein, refers to a region of a molecule or molecular complex, that, as a result of its shape, favorably associates with another chemical entity. Thus, a binding pocket may include or consist of features such as cavities, surfaces, or interfaces between domains. Chemical entities that may associate with a binding pocket include, but are not limited to, cofactors, substrates, inhibitors, agonists, and antagonists.

The amino acid constituents of a human BACE binding pocket as defined herein are positioned in three dimensions in accordance with the structure coordinates listed in Table 1 or Table 2. In one aspect, the structure coordinates defining a binding pocket of human BACE include structure coordinates of all atoms in the constituent amino acids; in another aspect, the structure coordinates of a binding pocket include structure coordinates of just the backbone atoms of the constituent amino acids.

The binding pocket of human BACE may include the amino acids listed in Table 4A, more preferably the amino acids listed in Table 5A, and most preferably the amino acids listed in Table 6A, as represented by the structure coordinates listed in Table 1. The binding pocket of human BACE may include the amino acids listed in Table 4B, more preferably the amino acids listed in Table 5B, and most preferably the amino acids listed in Table 6B, as represented by the structure coordinates listed in Table 2. Alternatively, the binding pocket of human BACE may be defined by those amino acids whose backbone atoms are situated within about 4 Å, more preferably within about 7 Å, most preferably within about 10 Å, of one or more constituent atoms of a bound substrate or modifier. In yet another alternative, the binding pocket may be defined by those amino acids whose backbone atoms are situated within a sphere centered on the coordinates representing the alpha carbon atom of residue Thr 231, the sphere having a radius of about 15 Å, preferably about 20 Å, and more preferably about 25 Å.

The term "BACE-like binding pocket" refers to a portion of a molecule or molecular complex whose shape is sufficiently similar to at least a portion of a binding pocket of human BACE as to be expected to bind related structural analogues. As used herein, "at least a portion" means that at least about 50% of the amino acids are included, preferably at least about 70% of the amino acids are included, more preferably at least about 90% of the amino acids are included, and most preferably all the amino acids are included. A structurally equivalent binding pocket is defined by a root mean square deviation from the structure coordinates of the backbone atoms of the amino acids that make up binding pockets in human BACE (as set forth in Table 1 or Table 2) of at most about 0.35 Å. How this calculation is obtained is described below.

Accordingly, the invention provides molecules or molecular complexes including a human BACE binding pocket or BACE-like binding pocket, as defined by the sets of structure coordinates described above.

TABLE 4A

Residues with 4 Å of the binding site for the P2$_1$ crystal form.

| | | | |
|---|---|---|---|
| GLY 11 | GLY 13 | LEU 30 | ASP 32 |
| GLY 34 | SER 35 | PRO 70 | TYR 71 |
| THR 72 | GLN 73 | GLY 74 | PHE 108 |
| ILE 110 | TRP 115 | TYR 198 | ILE 226 |
| ASP 228 | GLY 230 | THR 231 | THR 232 |
| ARG 235 | | | |

TABLE 4B

Residues within 4 Å of the binding site for the C2 crystal form.

| | | | |
|---|---|---|---|
| GLY 11 | GLY 12 | GLY 13 | LEU 30 |
| ASP 32 | GLY 34 | SER 35 | PRO 70 |
| TYR 71 | THR 72 | GLN 73 | GLY 74 |
| PHE 108 | ILE 110 | TRP 115 | TYR 198 |
| ASP 228 | GLY 230 | THR 231 | THR 232 |
| ARG 235 | | | |

TABLE 5A

Residues with 7 Å of the binding site for the P2$_1$ crystal form.

| | | | |
|---|---|---|---|
| GLY 11 | GLN 12 | GLY 13 | TYR 14 |
| LEU 30 | VAL 31 | ASP 32 | THR 33 |
| GLY 34 | SER 35 | SER 36 | ASN 37 |
| VAL 69 | PRO 70 | TYR 71 | THR 72 |
| GLN 73 | GLY 74 | LYS 75 | TRP 76 |
| ASP 106 | LYS 107 | PHE 108 | PHE 109 |
| ILE 110 | TRP 115 | ILE 118 | GLY 120 |
| ILE 126 | ALA 127 | ARG 128 | TYR 198 |
| LYS 224 | ILE 226 | ASP 228 | SER 229 |
| GLY 230 | THR 231 | THR 232 | ASN 233 |
| ARG 235 | SER 325 | THR 329 | VAL 332 |
| ALA 335 | | | |

TABLE 5B

Residues within 7 Å of the binding site for the C2 crystal form.

| | | | |
|---|---|---|---|
| LYS 9 | GLY 11 | GLN 12 | GLY 13 |
| TYR 14 | LEU 30 | ASP 32 | THR 33 |
| GLY 34 | SER 35 | SER 36 | ASN 37 |
| VAL 69 | PRO 70 | TYR 71 | THR 72 |
| GLN 73 | GLY 74 | LYS 75 | TRP 76 |
| ASP 106 | LYS 107 | PHE 108 | PHE 109 |
| ILE 110 | TRP 115 | ILE 118 | ILE 126 |
| ALA 127 | ARG 128 | TYR 198 | LYS 224 |
| ILE 226 | ASP 228 | SER 229 | GLY 230 |
| THR 231 | THR 232 | ASN 233 | ARG 235 |
| SER 325 | GLN 326 | THR 329 | VAL 332 |
| ALA 335 | | | |

TABLE 6A

Residues with 10 Å of binding site for the P2$_1$ crystal form.

| | | | |
|---|---|---|---|
| ARG 7 | GLY 8 | LYS 9 | SER 10 |
| GLY 11 | GLN 12 | GLY 13 | TYR 14 |
| TYR 15 | ILE 29 | LEU 30 | VAL 31 |
| ASP 32 | THR 33 | GLY 34 | SER 35 |

TABLE 6A-continued

Residues with 10 Å of binding site for the P2₁ crystal form.

| | | | |
|---|---|---|---|
| SER 36 | ASN 37 | PHE 38 | TYR 68 |
| VAL 69 | PRO 70 | TYR 71 | THR 72 |
| GLN 73 | GLY 74 | LYS 75 | TRP 76 |
| ILE 102 | SER 105 | ASP 106 | LYS 107 |
| PHE 108 | PHE 109 | ILE 110 | ASN 111 |
| SER 113 | TRP 115 | GLU 116 | GLY 117 |
| ILE 118 | LEU 119 | GLY 120 | LEU 121 |
| ALA 122 | TYR 123 | ALA 124 | GLU 125 |
| ILE 126 | ALA 127 | ARG 128 | PRO 129 |
| LEU 154 | TRP 197 | TYR 198 | TYR 199 |
| ASP 223 | LYS 224 | SER 225 | ILE 226 |
| VAL 227 | ASP 228 | SER 229 | GLY 230 |
| THR 231 | THR 232 | ASN 233 | LEU 234 |
| ARG 235 | LEU 236 | GLY 264 | ARG 307 |
| LYS 321 | PHE 322 | ALA 323 | ILE 324 |
| SER 325 | GLN 326 | SER 327 | SER 328 |
| THR 329 | GLY 330 | THR 331 | VAL 332 |
| MET 333 | GLY 334 | ALA 335 | VAL 336 |
| GLU 339 | | | |

TABLE 6B

Residues within 10 Å of the binding site for the C2 crystal form.

| | | | |
|---|---|---|---|
| ARG 7 | GLY 8 | LYS 9 | SER 10 |
| GLY 11 | GLN 12 | GLY 13 | TYR 14 |
| TYR 15 | ILE 29 | LEU 30 | VAL 31 |
| ASP 32 | THR 33 | GLY 34 | SER 35 |
| SER 36 | ASN 37 | PHE 38 | PHE 47 |
| TYR 68 | VAL 69 | PRO 70 | TYR 71 |
| THR 72 | GLN 73 | GLY 74 | LYS 75 |
| TRP 76 | ILE 102 | SER 105 | ASP 106 |
| LYS 107 | PHE 108 | PHE 109 | ILE 110 |
| ASN 111 | SER 113 | ASN 114 | TRP 115 |
| GLU 116 | GLY 117 | ILE 118 | LEU 119 |
| GLY 120 | LEU 121 | ALA 122 | TYR 123 |
| ALA 124 | GLU 125 | ILE 126 | ALA 127 |
| ARG 128 | PRO 129 | LEU 154 | LEU 167 |
| VAL 170 | TRP 197 | TYR 198 | TYR 199 |
| ASP 223 | LYS 224 | SER 225 | ILE 226 |
| VAL 227 | ASP 228 | SER 229 | GLY 230 |
| THR 231 | THR 232 | ASN 233 | LEU 234 |
| ARG 235 | LEU 236 | GLY 264 | ARG 307 |
| LYS 321 | ALA 323 | ILE 324 | SER 325 |
| GLN 326 | SER 327 | SER 328 | THR 329 |
| GLY 330 | THR 331 | VAL 332 | MET 333 |
| GLY 334 | ALA 335 | VAL 336 | GLU 339 |

Three-Dimensional Configurations

X-ray structure coordinates define a unique configuration of points in space. Those of skill in the art understand that a set of structure coordinates for protein or a protein/ligand complex, or a portion thereof, define a relative set of points that, in turn, define a configuration in three dimensions. A similar or identical configuration can be defined by an entirely different set of coordinates, provided the distances and angles between coordinates remain essentially the same. In addition, a scalable configuration of points can be defined by increasing or decreasing the distances between coordinates by a scalar factor while keeping the angles essentially the same.

The present invention thus includes the scalable three-dimensional configuration of points derived from the structure coordinates of at least a portion of a human BACE molecule or molecular complex, as listed in Table 1 and Table 2, as well as structurally equivalent configurations, as described below. Preferably, the scalable three-dimensional configuration includes points derived from structure coordinates representing the locations of a plurality of the amino acids defining a human BACE binding pocket.

In one embodiment, the scalable three-dimensional configuration includes points derived from structure coordinates representing the locations the backbone atoms of a plurality of amino acids defining the human BACE binding pocket, preferably the amino acids listed in Table 4A or 4B, more preferably the amino acids listed in Table 5A or 5B, and most preferably the amino acids listed in Table 6A or 6B. Alternatively, the scalable three-dimensional configuration includes points derived from structure coordinates representing the locations of the side chain and the backbone atoms (other than hydrogens) of a plurality of the amino acids defining the human BACE binding pocket, preferably the amino acids listed in Table 4A or 4B, more preferably the amino acids listed in Table 5A or 5B, and most preferably the amino acids listed in Table 6A or 6B.

Likewise, the invention also includes the scalable three-dimensional configuration of points derived from structure coordinates of molecules or molecular complexes that are structurally homologous to BACE, as well as structurally equivalent configurations. Structurally homologous molecules or molecular complexes are defined below. Advantageously, structurally homologous molecules can be identified using the structure coordinates of human BACE according to a method of the invention.

The configurations of points in space derived from structure coordinates according to the invention can be visualized as, for example, a holographic image, a stereodiagram, a model, or a computer-displayed image, and the invention thus includes such images, diagrams or models.

Structurally Equivalent Crystal Structures

Various computational analyses can be used to determine whether a molecule or a binding pocket portion thereof is "structurally equivalent," defined in terms of its three-dimensional structure, to all or part of human BACE or its binding pockets. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. The procedure used in Molecular Similarity to compare structures is divided into four steps: (1) load the structures to be compared; (2) define the atom equivalences in these structures; (3) perform a fitting operation; and (4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention equivalent atoms are defined as protein backbone atoms (N, Cα, C, and O) for all conserved residues between the two structures being compared. A conserved residue is defined as a residue which is structurally or functionally equivalent. Only rigid fitting operations are considered.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by QUANTA.

Machine Readable Storage Media

Transformation of the structure coordinates for all or a portion of human BACE or the human BACE/ligand complex or one of its binding pockets, for structurally homologous molecules as defined below, or for the structural equivalents of any of these molecules or molecular complexes as defined above, into three-dimensional graphical representations of the molecule or complex can be conveniently achieved through the use of commercially-available software.

The invention thus further provides a machine-readable storage medium including a data storage material encoded with machine readable data which, when using a machine programmed with instructions for using said data, displays a graphical three-dimensional representation of any of the molecule or molecular complexes of this invention that have been described above. In a preferred embodiment, the machine-readable data storage medium includes a data storage material encoded with machine readable data which, when using a machine programmed with instructions for using said data, displays a graphical three-dimensional representation of a molecule or molecular complex including all or any parts of a human BACE binding pocket or an BACE-like binding pocket, as defined above. In another preferred embodiment, the machine-readable data storage medium includes a data storage material encoded with machine readable data which, when using a machine programmed with instructions for using said data, displays a graphical three-dimensional representation of a molecule or molecular complex defined by the structure coordinates of all of the amino acids listed in Table 1 or Table 2, ± a root mean square deviation from the backbone atoms of said amino acids of less than about 0.65 Å.

In an alternative embodiment, the machine-readable data storage medium includes a data storage material encoded with a first set of machine readable data which includes the Fourier transform of the structure coordinates set forth in Table 1 or Table 2, and which, when using a machine programmed with instructions for using said data, can be combined with a second set of machine readable data including the x-ray diffraction pattern of a molecule or molecular complex to determine at least a portion of the structure coordinates corresponding to the second set of machine readable data.

For example, a system for reading a data storage medium may include a computer including a central processing unit ("CPU"), a working memory which may be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, track balls, touch pads, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this invention may be inputted via the use of a modem or modems connected by a telephone line or dedicated data line. Alternatively or additionally, the input hardware may include CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of a binding pocket of this invention using a program such as QUANTA as described herein. Output hardware might also include a printer, so that hard copy output may be produced, or a disk drive, to store system output for later use.

In operation, a CPU coordinates the use of the various input and output devices, coordinates data accesses from mass storage devices, accesses to and from working memory, and determines the sequence of data processing steps. A number of programs may be used to process the machine-readable data of this invention. Such programs are discussed in reference to the computational methods of drug discovery as described herein. References to components of the hardware system are included as appropriate throughout the following description of the data storage medium.

Machine-readable storage devices useful in the present invention include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

Structurally Homologous Molecules, Molecular Complexes, and Crystal Structures

The structure coordinates set forth in Table 1 or Table 2 can be used to aid in obtaining structural information about another crystallized molecule or molecular complex. The method of the invention allows determination of at least a portion of the three-dimensional structure of molecules or molecular complexes which contain one or more structural features that are similar to structural features of human BACE. These molecules are referred to herein as "structurally homologous" to human beta secretase. Similar structural features can include, for example, regions of amino acid identity, conserved active site or binding site motifs, and similarly arranged secondary structural elements (e.g., α helices and β sheets). Optionally, structural homology is determined by aligning the residues of the two amino acid sequences to optimize the number of identical amino acids along the lengths of their sequences; gaps in either or both sequences are permitted in making the alignment in order to optimize the number of identical amino acids, although the amino acids in each sequence must nonetheless remain in their proper order. Preferably, two amino acid sequences are compared using the Blastp program, version 2.0.9, of the BLAST 2 search algorithm, as described by Tatusova et al., *FEMS Microbiol Lett* 174, 247-50 (1999). Preferably, the default values for all BLAST 2 search parameters are used, including matrix=BLOSUM62; open gap penalty=11, extension gap penalty=1, gap x_dropoff=50, expect=10, wordsize=3, and filter on. In the comparison of two amino acid sequences using the BLAST search algorithm, structural similarity is referred to as "identity." Preferably, a structurally homologous molecule is a protein that has an amino acid sequence sharing at least 65% identity with a native or recombinant amino acid sequence of human BACE (for example, SEQ ID NO:1). More preferably, a protein that is structurally homologous to human BACE includes at least one contiguous stretch of at least 50 amino acids that shares at least 80% amino acid sequence identity with the analogous portion of the native or recombinant human BACE (for example, SEQ ID NO:1, SEQ ID NO:2, and SEQ ID NO:3). Methods for generating structural information about the structurally homologous molecule or molecular complex are well-known and include, for example, molecular replacement techniques.

Therefore, in another embodiment this invention provides a method of utilizing molecular replacement to obtain structural information about a molecule or molecular complex whose structure is unknown including the steps of:

(a) crystallizing the molecule or molecular complex of unknown structure;

(b) generating an x-ray diffraction pattern from said crystallized molecule or molecular complex; and (c) applying at least a portion of the structure coordinates set forth in Table 1 to the x-ray diffraction pattern to generate a three-dimensional electron density map of the molecule or molecular complex whose structure is unknown.

By using molecular replacement, all or part of the structure coordinates of human BACE or the human BACE/ligand complex as provided by this invention can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a structurally homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of human BACE or the human BACE/modifier complex within the unit cell of the crystal of the unknown molecule or molecular complex so as best to account for the observed x-ray diffraction pattern of the crystal of the molecule or molecular complex whose structure is unknown. Phases can then be calculated from this model and combined with the observed x-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (Lattman, *Meth. Enzymol.*, 115:55-77 (1985); M. G. Rossman, ed., "The Molecular Replacement Method," *Int. Sci. Rev. Ser.*, No. 13, Gordon & Breach, New York (1972)).

Structural information about a portion of any crystallized molecule or molecular complex that is sufficiently structurally homologous to a portion of human BACE can be resolved by this method. In addition to a molecule that shares one or more structural features with human BACE as described above, a molecule that has similar bioactivity, such as the same catalytic activity, substrate specificity or ligand binding activity as human BACE, may also be sufficiently structurally homologous to human BACE to permit use of the structure coordinates of human BACE to solve its crystal structure.

In a preferred embodiment, the method of molecular replacement is utilized to obtain structural information about a molecule or molecular complex, wherein the molecule or molecular complex includes a human BACE subunit or homolog. A "subunit" of human BACE is a human BACE molecule that has been truncated at the N-terminus or the C-terminus, or both. In the context of the present invention, a "homolog" of human BACE is a protein that contains one or more amino acid substitutions, deletions, additions, or rearrangements with respect to the amino acid sequence of human BACE (SEQ ID NO:1, SEQ ID NO:2, and SEQ ID NO:3), but that, when folded into its native conformation, exhibits or is reasonably expected to exhibit at least a portion of the tertiary (three-dimensional) structure of human BACE. For example, structurally homologous molecules can contain deletions or additions of one or more contiguous or noncontiguous amino acids, such as a loop or a domain. Structurally homologous molecules also include "modified" human BACE molecules that have been chemically or enzymatically derivatized at one or more constituent amino acid, including side chain modifications, backbone modifications, and N- and C-terminal modifications including acetylation, hydroxylation, methylation, amidation, and the attachment of carbohydrate or lipid moieties, cofactors, and the like.

A heavy atom derivative of human BACE is also included as a human BACE homolog. The term "heavy atom derivative" refers to derivatives of human BACE produced by chemically modifying a crystal of human BACE. In practice, a crystal is soaked in a solution containing heavy metal atom salts, or organometallic compounds, e.g., lead chloride, gold thiomalate, thiomersal or uranyl acetate, which can diffuse through the crystal and bind to the surface of the protein. The location(s) of the bound heavy metal atom(s) can be determined by x-ray diffraction analysis of the soaked crystal. This information, in turn, is used to generate the phase information used to construct three-dimensional structure of the protein (T. L. Blundell and N. L. Johnson, *Protein Crystallography*, Academic Press (1976)).

Because human BACE can crystallize in more than one crystal form, the structure coordinates of human BACE as provided by this invention are particularly useful in solving the structure of other crystal forms of human BACE or human BACE complexes.

The structure coordinates of human BACE as provided by this invention are particularly useful in solving the structure of human BACE mutants. Mutants may be prepared, for example, by expression of human BACE cDNA previously altered in its coding sequence by oligonucleotide-directed mutagenesis. Mutants may also be generated by site-specific incorporation of unnatural amino acids into BACE proteins using the general biosynthetic method of Noren et al., *Science*, 244:182-88 (1989). In this method, the codon encoding the amino acid of interest in wild-type human BACE is replaced by a "blank" nonsense codon, TAG, using oligonucleotide-directed mutagenesis. A suppressor tRNA directed against this codon is then chemically aminoacylated in vitro with the desired unnatural amino acid. The aminoacylated tRNA is then added to an in vitro translation system to yield a mutant human BACE with the site-specific incorporated unnatural amino acid.

Selenocysteine or selenomethionine may be incorporated into wild-type or mutant human BACE by expression of human BACE-encoding cDNAs in auxotrophic *E. coli* strains (Hendrickson et al., *EMBO J.*, 9:1665-72 (1990)). In this method, the wild-type or mutagenized human BACE cDNA may be expressed in a host organism on a growth medium depleted of either natural cysteine or methionine (or both) but enriched in selenocysteine or selenomethionine (or both). Alternatively, selenomethionine analogues may be prepared by down regulation methionine biosynthesis. (Benson et al., *Nat. Struct. Biol.*, 2:644-53 (1995); Van Duyne et al., *J. Mol. Biol.*, 229:105-24 (1993)).

The structure coordinates of human BACE listed in Table 1 and Table 2 are also particularly useful to solve the structure of crystals of human BACE, human BACE mutants or human BACE homologs co-complexed with a variety of chemical entities. This approach enables the determination of the optimal sites for interaction between chemical entities, including candidate human BACE modifiers and human BACE. Potential sites for modification within the various binding sites of the molecule can also be identified. This information provides an additional tool for determining the most efficient binding interactions, for example, increased hydrophobic interactions, between human BACE and a chemical entity. For example, high resolution x-ray diffraction data collected from crystals exposed to different types of solvent allows the determination of where each type of solvent molecule resides. Small molecules that bind tightly to those sites can then be designed and synthesized and tested for their potential human BACE inhibition activity.

All of the complexes referred to above may be studied using well-known x-ray diffraction techniques and may be refined versus 1.5-3.5 Å resolution x-ray data to an R value of about 0.30 or less using computer software, such as X-PLOR (Yale University, 81992, distributed by Molecular Simulations, Inc.; see, e.g., Blundell & Johnson, supra; *Meth. Enzymol.*, Vol. 114 & 115, H. W. Wyckoff et al., eds., Academic Press (1985)). This information may thus be used to optimize known human BACE modifiers, and more importantly, to design new human BACE modifiers.

The invention also includes the unique three-dimensional configuration defined by a set of points defined by the structure coordinates for a molecule or molecular complex structurally homologous to human BACE as determined using the method of the present invention, structurally equivalent configurations, and magnetic storage media including such set of structure coordinates.

Further, the invention includes structurally homologous molecules as identified using the method of the invention.

Homology Modeling

Using homology modeling, a computer model of a human BACE homolog can be built or refined without crystallizing the homolog. First, a preliminary model of the human BACE homolog is created by sequence alignment with human BACE, secondary structure prediction, the screening of structural libraries, or any combination of those techniques. Computational software may be used to carry out the sequence alignments and the secondary structure predictions. Structural incoherences, e.g., structural fragments around insertions and deletions, can be modeled by screening a structural library for peptides of the desired length and with a suitable conformation. For prediction of the side chain conformation, a side chain rotamer library may be employed. If the human BACE homolog has been crystallized, the final homology model can be used to solve the crystal structure of the homolog by molecular replacement, as described above. Next, the preliminary model is subjected to energy minimization to yield an energy minimized model. The energy minimized model may contain regions where stereochemistry restraints are violated, in which case such regions are remodeled to obtain a final homology model. The homology model is positioned according to the results of molecular replacement, and subjected to further refinement including molecular dynamics calculations.

Rational Drug Design

Computational techniques can be used to screen, identify, select and/or design chemical entities capable of associating with human BACE or structurally homologous molecules. Knowledge of the structure coordinates for human BACE permits the design and/or identification of synthetic compounds and/or other molecules which have a shape complementary to the conformation of the human BACE binding site. In particular, computational techniques can be used to identify or design chemical entities, such as inhibitors, agonists and antagonists, that associate with a human BACE binding pocket or an BACE-like binding pocket. Potential modifiers may bind to or interfere with all or a portion of an active site of human BACE, and can be competitive, non-competitive, or uncompetitive inhibitors; or interfere with dimerization by binding at the interface between the two monomers. Once identified and screened for biological activity, these inhibitors/agonists/antagonists may be used therapeutically or prophylactically to block human BACE activity and, thus, prevent the onset and/or further progression of Alzheimer's disease. Structure-activity data for analogues of ligands that bind to or interfere with human BACE or BACE-like binding pockets can also be obtained computationally.

The term "chemical entity," as used herein, refers to chemical compounds, complexes of two or more chemical compounds, and fragments of such compounds or complexes. Chemical entities that are determined to associate with human BACE are potential drug candidates. Data stored in a machine-readable storage medium that displays a graphical three-dimensional representation of the structure of human BACE or a structurally homologous molecule, as identified herein, or portions thereof may thus be advantageously used for drug discovery. The structure coordinates of the chemical entity are used to generate a three-dimensional image that can be computationally fit to the three-dimensional image of human BACE or a structurally homologous molecule. The three-dimensional molecular structure encoded by the data in the data storage medium can then be computationally evaluated for its ability to associate with chemical entities. When the molecular structures encoded by the data is displayed in a graphical three-dimensional representation on a computer screen, the protein structure can also be visually inspected for potential association with chemical entities.

One embodiment of the method of drug design involves evaluating the potential association of a known chemical entity with human BACE or a structurally homologous molecule, particularly with a human BACE binding, pocket or BACE-like binding pocket. The method of drug design thus includes computationally evaluating the potential of a selected chemical entity to associate with any of the molecules or molecular complexes set forth above. This method includes the steps of: (a) employing computational means to perform a fitting operation between the selected chemical entity and a binding pocket or a pocket nearby the binding pocket of the molecule or molecular complex; and (b) analyzing the results of said fitting operation to quantify the association between the chemical entity and the binding pocket.

In another embodiment, the method of drug design involves computer-assisted design of chemical entities that associate with human BACE, its homologs, or portions thereof. Chemical entities can be designed in a step-wise fashion, one fragment at a time, or may be designed as a whole or "de novo."

To be a viable drug candidate, the chemical entity identified or designed according to the method must be capable of structurally associating with at least part of a human BACE or BACE-like binding pockets, and must be able, sterically and energetically, to assume a conformation that allows it to associate with the human BACE or BACE-like binding pocket. Non-covalent molecular interactions important in this association include hydrogen bonding, van der Waals interactions, hydrophobic interactions, and electrostatic interactions. Conformational considerations include the overall three-dimensional structure and orientation of the chemical entity in relation to the binding pocket, and the spacing between various functional groups of an entity that directly interact with the BACE-like binding pocket or homologs thereof.

Optionally, the potential binding of a chemical entity to a human BACE or BACE-like binding pocket is analyzed using computer modeling techniques prior to the actual synthesis and testing of the chemical entity. If these computational experiments suggest insufficient interaction and association between it and the human BACE or BACE-like binding pocket, testing of the entity is obviated. However, if computer modeling indicates a strong interaction, the molecule may then be synthesized and tested for its ability to bind to or interfere with a human BACE or BACE-like binding pocket. Binding assays to determine if a compound (e.g., an inhibitor) actually interferes with human BACE can also be performed and are well known in the art. Binding assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof.

One method for determining whether a modifier binds to a protein is isothermal denaturation. This method includes taking a sample of a protein (in the presence or absence of substrates) at a fixed elevated temperature where denaturation of the protein occurs in a given time frame, adding the chemical entity to the protein, and monitoring the rate of denaturation. If the chemical entity does bind to the protein, it is expected that the rate of denaturation would be slower in the presence of the chemical entity than in the absence of the chemical entity. For example, this method has been described in Epps et al., *Anal. Biochem.*, 292:40-50 (2001).

One skilled in the art may use one of several methods to screen chemical entities or fragments for their ability to associate with a human BACE or BACE-like binding pocket. This process may begin by visual inspection of, for example, a human BACE or BACE-like binding pocket on the computer screen based on the human BACE structure coordinates listed in Table 1 or other coordinates which define a similar shape generated from the machine-readable storage medium. Selected fragments or chemical entities may then be positioned in a variety of orientations, or docked, within the binding pocket. Docking may be accomplished using software such as QUANTA and SYBYL, followed by energy minimization and molecular dynamics with standard molecular mechanics forcefields, such as CHARMM and AMBER.

Specialized computer programs may also assist in the process of selecting fragments or chemical entities. Examples include GRID (Goodford, *J. Med. Chem.*, 28:849-57 (1985); available from Oxford University, Oxford, UK); MCSS (Miranker et al., *Proteins: Struct. Funct. Gen.*, 11:29-34 (1991); available from Molecular Simulations, San Diego, Calif.); AUTODOCK (Goodsell et al., *Proteins: Struct. Funct. Genet.*, 8:195-202 (1990); available from Scripps Research Institute, La Jolla, Calif.); and DOCK (Kuntz et al., *J. Mol. Biol.*, 161:269-88 (1982); available from University of California, San Francisco, Calif.).

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of human BACE. This would be followed by manual model building using software such as QUANTA or SYBYL (Tripos Associates, St. Louis, Mo.).

Useful programs to aid one of skill in the art in connecting the individual chemical entities or fragments include, without limitation, CAVEAT (P. A. Bartlett et al., in "Molecular Recognition: Chemical and Biological Problems," Special Publ., Royal Chem. Soc., 78:182-96 (1989); Lauri et al., *J. Comput. Aided Mol. Des.* 8:51-66 (1994); available from the University of California, Berkeley, Calif.); 3D database systems such as ISIS (available from MDL Information Systems, San Leandro, Calif.; reviewed in Martin, *J. Med. Chem.*, 35:2145-54 (1992)); and HOOK (Eisen et al., *Proteins: Struc., Funct., Genet.*, 19:199-221 (1994); available from Molecular Simulations, San Diego, Calif.).

Human BACE binding compounds may be designed "de novo" using either an empty binding site or optionally including some portion(s) of a known modifier(s). There are many de novo ligand design methods including, without limitation, LUDI (Böhm, *J. Comp. Aid. Molec. Design*, 6:61-78 (1992); available from Molecular Simulations Inc., San Diego, Calif.); LEGEND (Nishibata et al., *Tetrahedron*, 47:8985-90 (1991); available from Molecular Simulations Inc., San Diego, Calif.); LeapFrog (available from Tripos Associates, St. Louis, Mo.); and SPROUT (Gillet et al., *J. Comput. Aided Mol. Design*, 7:127-53 (1993); available from the University of Leeds, UK).

Once a compound has been designed or selected by the above methods, the efficiency with which that entity may bind to or interfere with a human BACE or BACE-like binding pocket may be tested and optimized by computational evaluation. For example, an effective human BACE or BACE-like binding pocket modifier must preferably demonstrate a relatively small difference in energy between its bound and free states (i.e., a small deformation energy of binding). Thus, the most efficient human BACE or BACE-like binding pocket modifiers should preferably be designed with a deformation energy of binding of at most about 10 kcal/mole; more preferably, at most 7 kcal/mole. Human BACE or BACE-like binding pocket modifiers may interact with the binding pocket in more than one conformation that is similar in overall binding energy. In those cases, the deformation energy of binding is taken to be the difference between the energy of the free entity and the average energy of the conformations observed when the modifier binds to the protein.

An entity designed or selected as binding to or interfering with a human BACE or BACE-like binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole, and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. 81995); AMBER, version 4.1 (P. A. Kollman, University of California at San Francisco, 81995); QUANTA/ CHARMM (Molecular Simulations, Inc., San Diego, Calif. 81995); Insight II/Discover (Molecular Simulations, Inc., San Diego, Calif. 81995); DelPhi (Molecular Simulations, Inc., San Diego, Calif. 81995); and AMSOL (Quantum Chemistry Program Exchange, Indiana University). These programs may be implemented, for instance, using a Silicon Graphics workstation such as an Indigo$^2$ with "IMPACT" graphics. Other hardware systems and software packages will be known to those skilled in the art.

Another approach encompassed by this invention is the computational screening of small molecule databases for chemical entities or compounds that can bind in whole, or in part, to a human BACE or BACE-like binding pocket. In this screening, the quality of fit of such entities to the binding site may be judged either by shape complementarity or by estimated interaction energy (Meng et al., *J. Comp. Chem.*, 13:505-24 (1992)).

This invention also enables the development of chemical entities that can isomerize to short-lived reaction intermediates in the chemical reaction of a substrate or other compound that interferes with or with human BACE. Time-dependent analysis of structural changes in human BACE during its interaction with other molecules is carried out. The reaction intermediates of human BACE can also be deduced from the reaction product in co-complex with human BACE. Such information is useful to design improved analogues of known human BACE modifiers or to design novel classes of modifiers based on the reaction intermediates of the human BACE and modifier co-complex. This provides a novel route for designing human BACE modifiers with both high specificity and stability.

Yet another approach to rational drug design involves probing the human BACE crystal of the invention with molecules including a variety of different functional groups to determine optimal sites for interaction between candidate human BACE modifiers and the protein. For example, high resolution x-ray diffraction data collected from crystals soaked in or co-crystallized with other molecules allows the determination of where each type of solvent molecule sticks. Molecules that bind tightly to those sites can then be further modified and synthesized and tested for their BACE modifier activity (Travis, *Science*, 262:1374 (1993)).

In a related approach, iterative drug design is used to identify modifiers of human BACE. Iterative drug design is a method for optimizing associations between a protein and a compound by determining and evaluating the three-dimensional structures of successive sets of protein/compound complexes. In iterative drug design, crystals of a series of protein/compound complexes are obtained and then the three-dimensional structures of each complex is solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affected the protein/compound associations, these associations may be optimized.

A compound that is identified or designed as a result of any of these methods can be obtained (or synthesized) and tested for its biological activity, e.g., inhibition of BACE activity.

Assay systems that can be used to demonstrate efficacy of the compound inhibitors of the invention are known. Representative assay systems are described, for example, in U.S. Pat. Nos. 5,942,400 (Anderson et al.) and 5,744,346 (Chrysler et al.).

Pharmaceutical Compositions (Modifiers)

Pharmaceutical compositions of this invention include a potential modifier of human BACE activity identified according to the invention, or a pharmaceutically acceptable salt thereof, and a pharmaceutically acceptable carrier, adjuvant, or vehicle. The term "pharmaceutically acceptable carrier" refers to a carrier(s) that is "acceptable" in the sense of being compatible with the other ingredients of a composition and not deleterious to the recipient thereof. Optionally, the pH of the formulation is adjusted with pharmaceutically acceptable acids, bases, or buffers to enhance the stability of the formulated compound or its delivery form.

Methods of making and using such pharmaceutical compositions are also included in the invention. The pharmaceutical compositions of the invention can be administered orally, parenterally, by inhalation spray, topically, rectally, nasally, buccally, vaginally, or via an implanted reservoir. Oral administration or administration by injection is preferred. The term parenteral as used herein includes subcutaneous, intracutaneous, intravenous, intramuscular, intra-articular, intrasynovial, intrasternal, intrathecal, intralesional, and intracranial injection or infusion techniques.

Dosage levels of about 0.01 to about 100 mg/kg body weight per day, preferably about 0.5 to about 75 mg/kg body weight per day of the human BACE inhibitory compounds described herein are useful for the prevention and treatment of human BACE mediated disease. Typically, the pharmaceutical compositions of this invention will be administered about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain about 5% to about 95% active compound (w/w). Preferably, such preparations contain about 20% to about 80% active compound.

In order that this invention be more fully understood, the following examples are set forth. These examples are for the purpose of illustration only and are not to be construed as limiting the scope of the invention in any way.

EXAMPLES

Example 1

Crystallization and Structure Determination of Human BACE in P2$_1$ Crystal Form Expression, Purification, and Crystallization Two BACE constructs, 1) pET11a-T7.Tag-Gly-Ser-Met-(A⁻GV . . . QTDES) (referred to as pET11a-BACE; SEQ ID NO:1) and 2) pQE80L-Met-Arg-Gly-Ser-(His)$_6$-Gly-Ser-Ile-Glu-Thr-Asp-(TQH . . . QTDES) (referred to as pQE80L-BACE; SEQ ID NO:2) were cloned and expressed as inclusion bodies. Inclusion bodies obtained from 10 liters of cell culture were washed one time in 10 mM TRIS buffer (pH 8.12) and 1 mM EDTA (TE). The inclusion bodies were extracted with 15-20 ml 8 M urea, 100 mM AMPSO, 1 mM glycine, 1 mM EDTA, and 100 mM β-Mercaptoethanol (BME, pH 10.5-10.8). After centrifugation, the protein concentration of the supernatant was adjusted by dilution with the above buffer to read approximately 5.0 at A$_{280}$. The protein was then diluted with 8 M urea, 100 mM AMPSO, 1 mM glycine, 1 mM EDTA, and the BME concentration adjusted to 10 mM by the addition of solid BME to read an $A_{280}$~0.5 and pH 10.5-10.8. The solution was centrifuged. The refolding worked best with AMPSO, however, the AMPSO could be substituted with CAPS or TRIS. Analysis of the sample in 8 M urea by SDS-PAGE revealed BACE as the major component of the solubilized inclusion bodies. BACE migrated as a band of Mr=50,000. Refolding was carried out by a 20-25 fold dilution with cold water (4-15° C.). Upon dilution, the pH dropped automatically to 9.5-10.2. The sample was then allowed to rest in the cold room. Activity assays were performed daily to monitor protein refolding. Results from various experiments indicated that maximal activity was usually reached at day 5.

Figure 2:
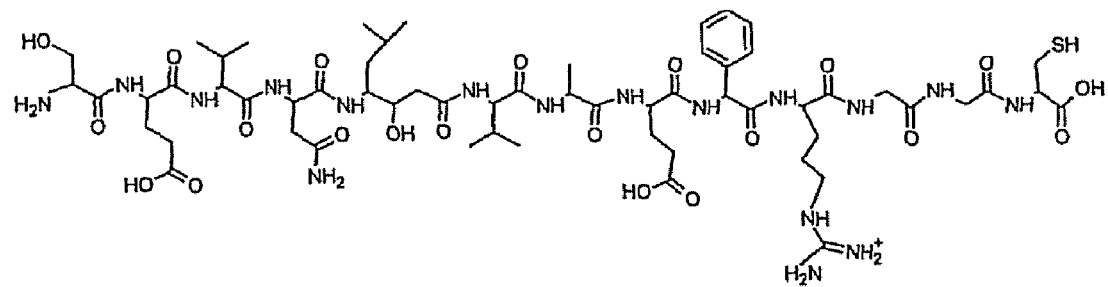
FIG. 2 is the synthetic peptide Ser-Glu-Val-Asn-Sta-Val-Ala-Glu-Phe-Arg-Gly-Gly-Cys (where Sta=statine) (SEQ ID NO:4) used for affinity purification of BACE.
Figure 3:
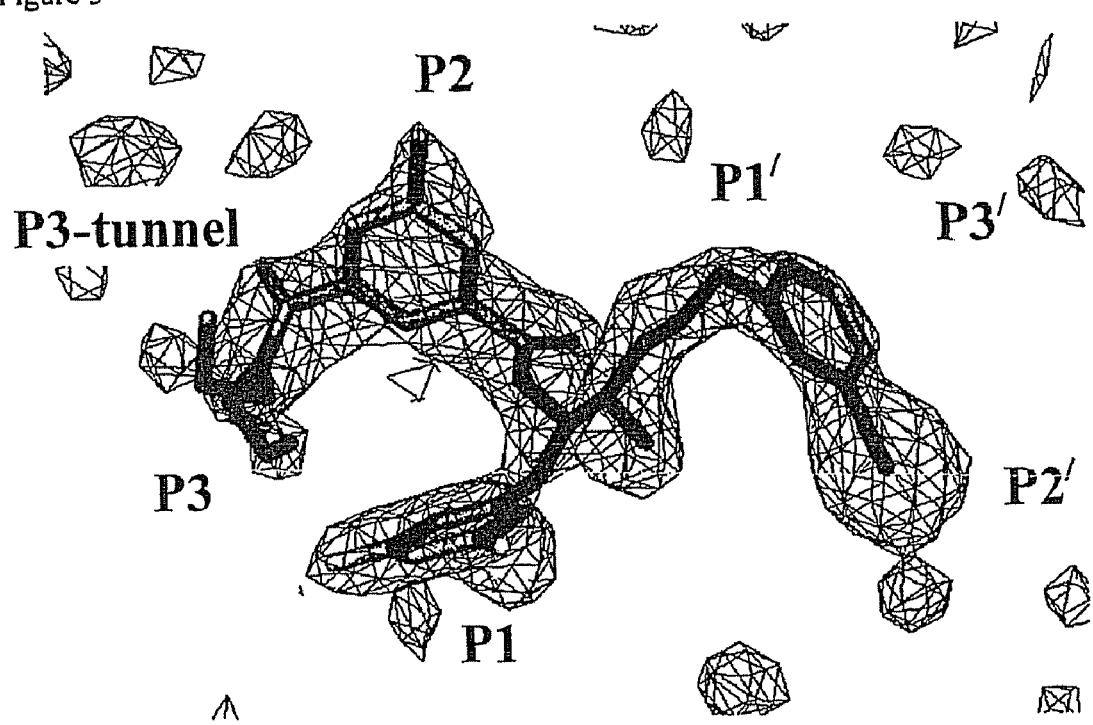
FIG. 3 is an Fo-Fc electron density map for the inhibitor illustrated in FIG. 1 at 2.15 Å contoured at 2σ for the $P2_1$ crystal form.
Figure 4:
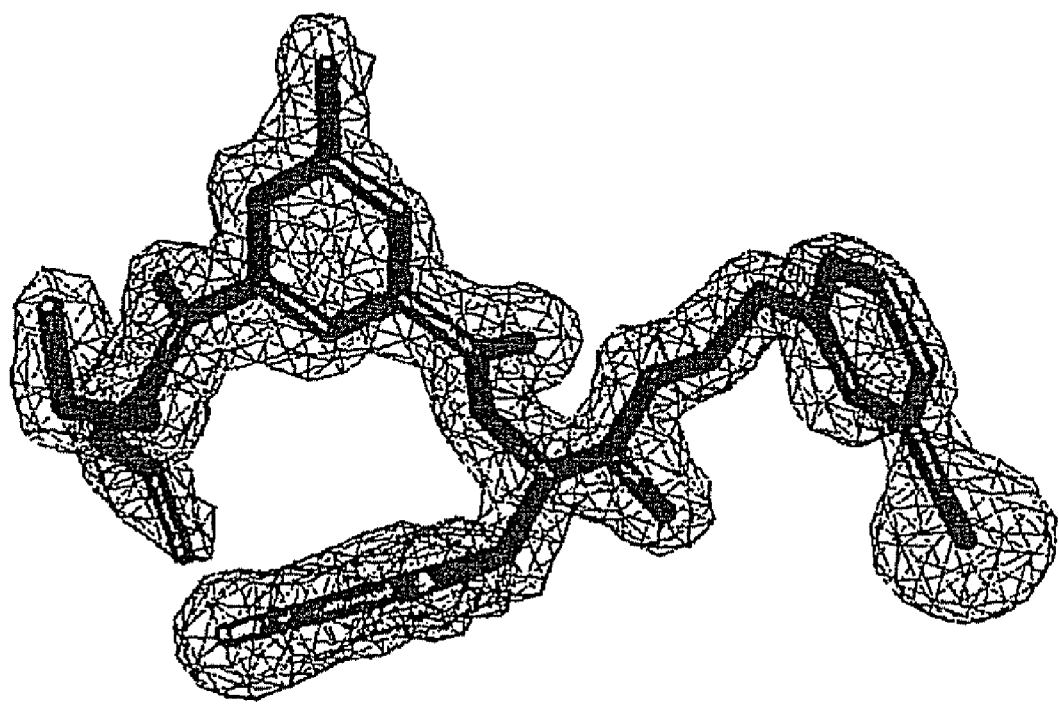
FIG. 4 is an Fo-Fc electron density map for the inhibitor illustrated in FIG. 1 at 1.7 Å contoured at 2σ for the C2 crystal form.
Figure 5:
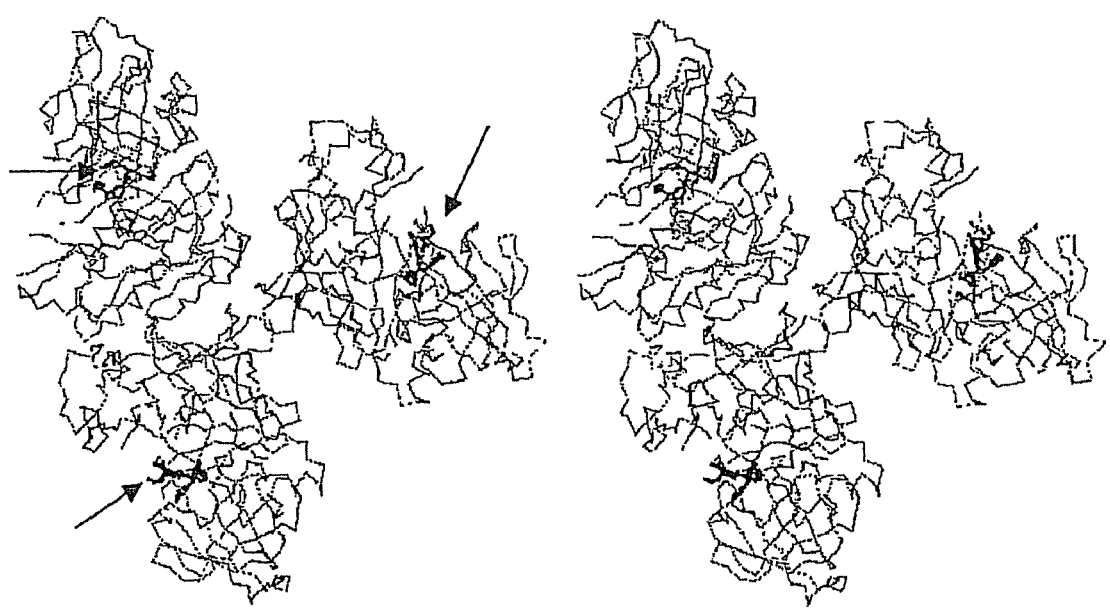
FIG. 5 is a stereo view of a $C^\alpha$ trace of three monomers in the asymmetric unit of the $P2_1$ crystal form of human BACE (grey line) in the presence of the inhibitor illustrated in FIG. 1. The inhibitor trace is indicated by a dark black line.
Figure 6:
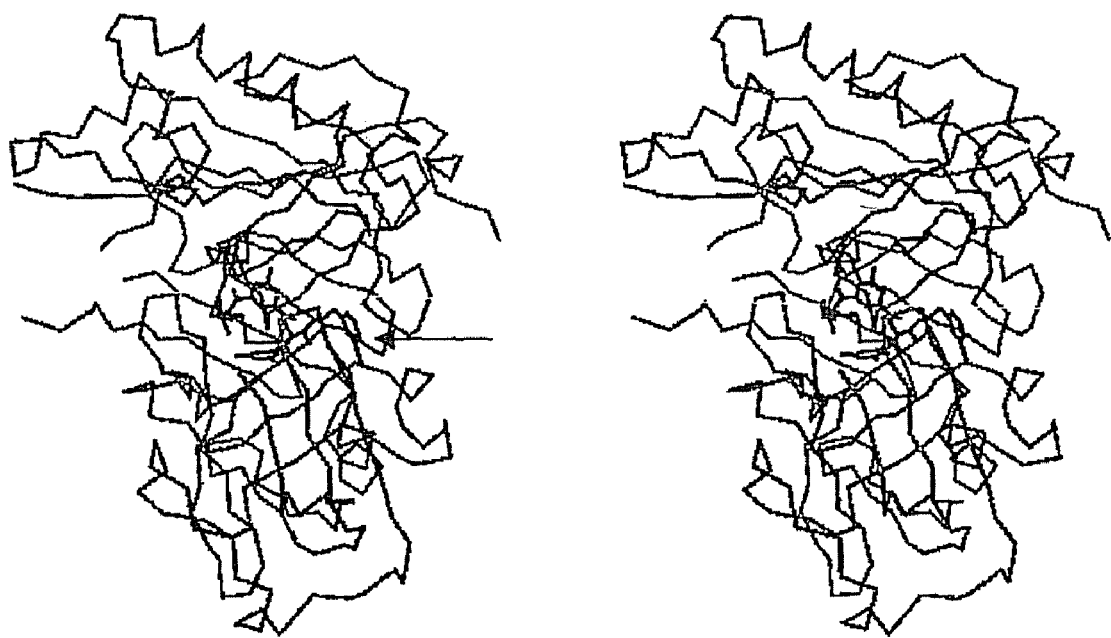
FIG. 6 is a stereo view of a $C^\alpha$ trace of one monomer in the asymmetric unit of the C2 crystal form of human BACE (grey line) in the presence of the inhibitor illustrated in FIG. 1. The general location of the inhibitor trace (black line) is indicated by an arrow.
Figure 7:
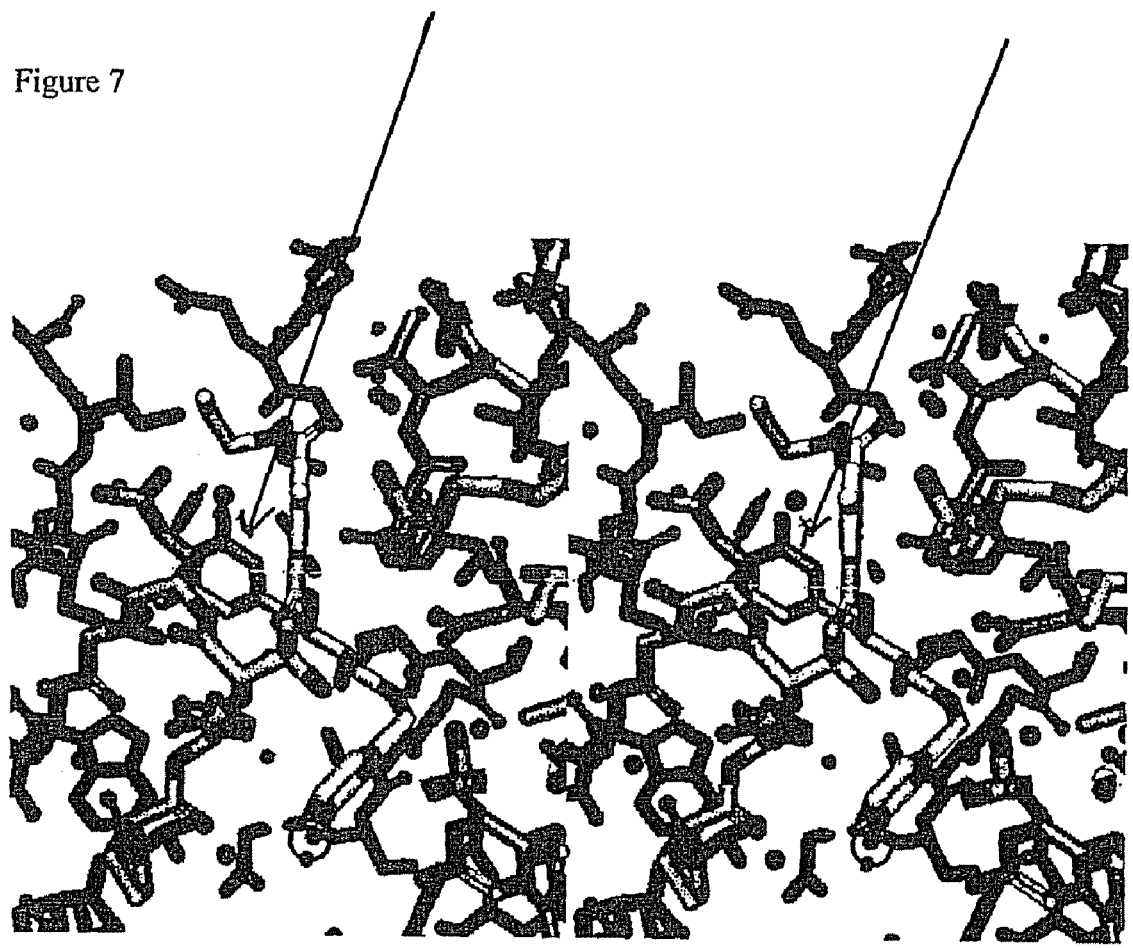
FIG. 7 depicts a stereo view of the active site of human BACE from the $P2_1$ crystal form (illustrated with light gray carbons, dark gray oxygens, and black nitrogens) with the inhibitor illustrated in FIG. 1. The general location of the inhibitor is indicated by an arrow (illustrated with light gray carbons, dark gray oxygens, and black nitrogens). The iodine atom is circled and the two fluorine atoms are indicated by a "•" symbol.
Figure 8:
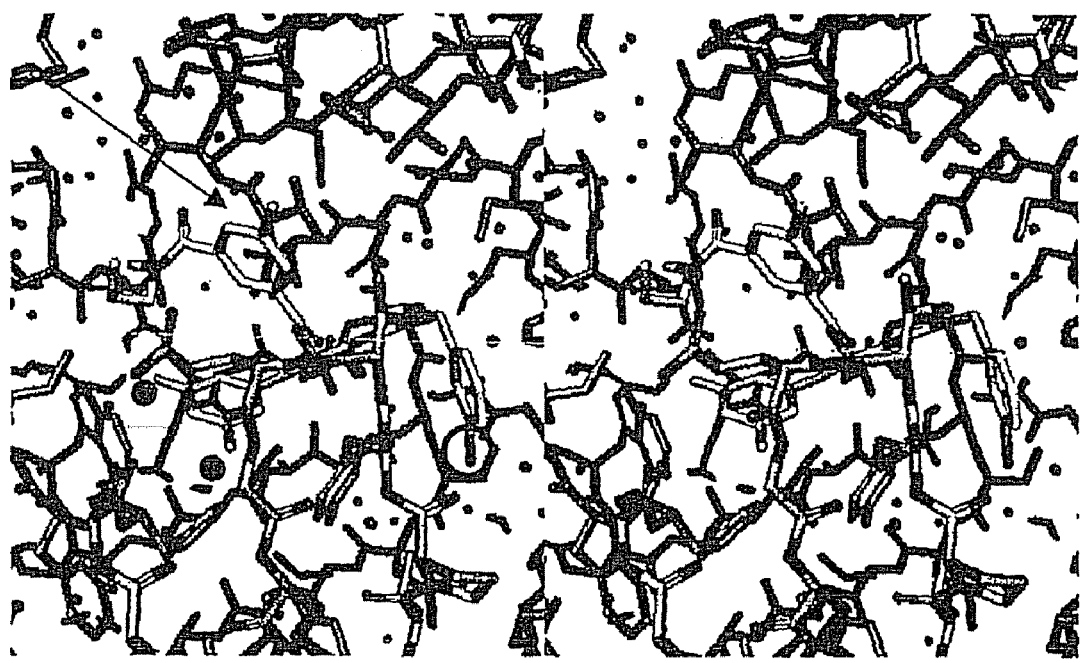
FIG. 8 depicts a stereo view of the active site of human BACE from the C2 crystal form (illustrated with light gray carbons, dark gray oxygens, and black nitrogens) with the inhibitor illustrated in FIG. 1. The general location of the inhibitor is indicated by an arrow (illustrated with light gray carbons, dark gray oxygens, and black nitrogens). The iodine atom is circled and the two fluorine atoms are indicated by a "•" symbol.
Figure 9:
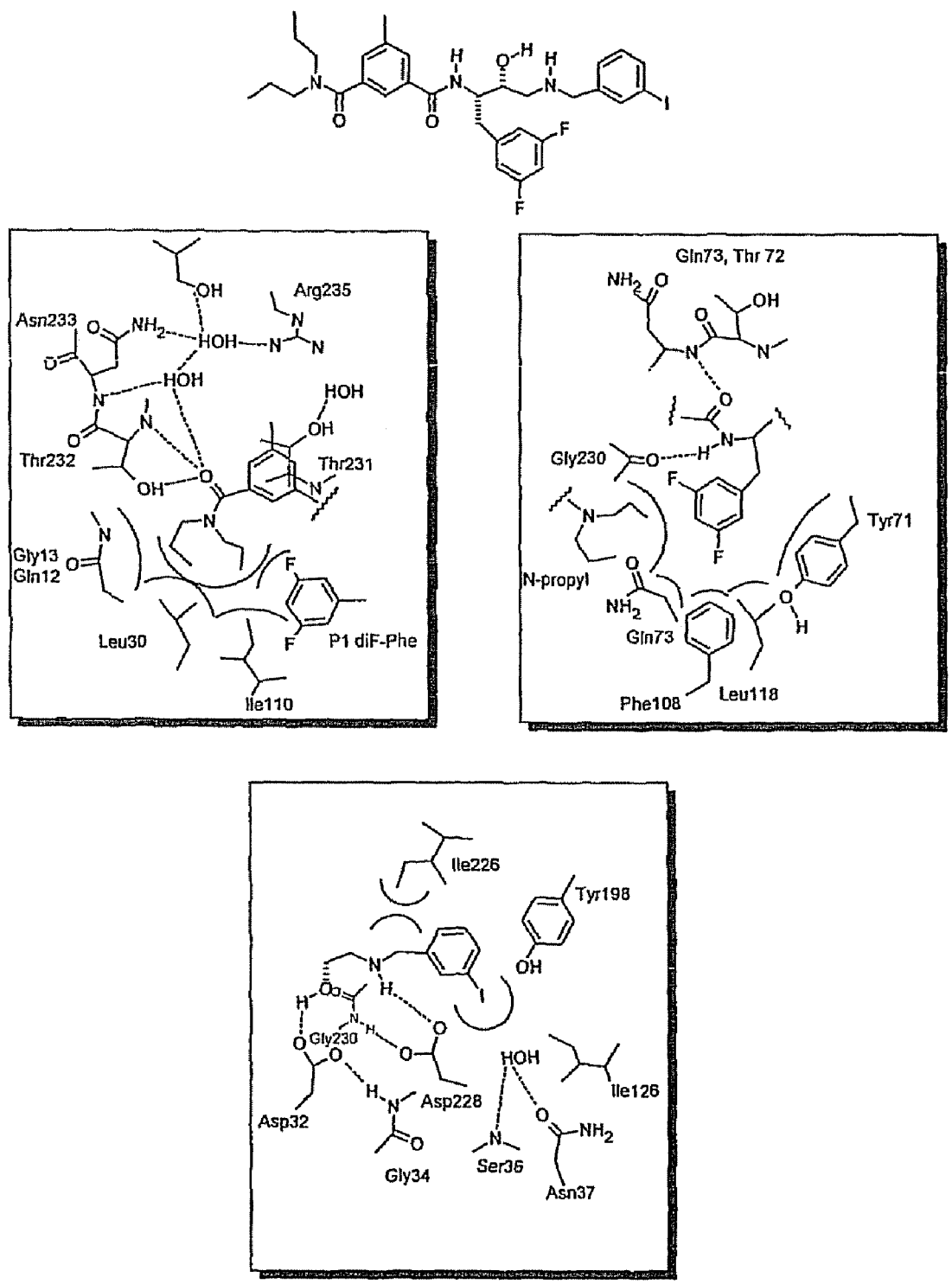
FIG. 9 depicts distance of the interactions between the inhibitor and the active site of BACE. Amino acid residues or main chain atoms within 3.5 Å of the inhibitor are shown. Van der Waals interactions are shown with arcs.

The pH of the refolded protein was lowered from about 10 to 8.5 with HCl and loaded onto a Q-Sepharose column (5.0 cm×2.8 cm). BACE was eluted with 0.75 M NaCl in 0.4 M Urea and 10 mM TRIS buffer (pH 8.2). After concentration, BACE was delivered onto a Sepbacryl-S200 column (2.5 cm×130 cm) equilibrated and eluted in 20 mM Hepes buffer and 100 mM NaCl (pH 8.0). This molecular sieving step resolved the active monomeric BACE from its aggregated forms. Finally, the sample was brought to pH 4.5 and applied to a 10 ml affinity column equilibrated at the same pH. The column was washed with 6 column volumes of 20 mM sodium acetate buffer (pH 4.5) and 150 mM NaCl. BACE was eluted at pH 8.5 in 0.1 M borate buffer. The resin had been cross-linked with the synthetic peptide shown in FIG. 2. This final step removed any residual contaminants. From 10 liter of *E. Coli* cell culture, the amount of protein obtained was 55 mg, and 93 mg of highly purified pET11a-BACE and pQE-80-BACE constructs, respectively.

Purified pET11a-BACE or pQE80L-BACE was dialyzed into 100 mM sodium borate (pH 8.5). Initial attempts to crystallize this material by incubation of inhibitors in a sparse matrix screen were unsuccessful. Dynamic light scattering data indicated that there was an aggregate species present that might interfere with crystallization. In an effort to reduce non-specific aggregation, the enzyme was concentrated in the presence of the inhibitor shown in FIG. 1. The purpose of this was two-fold: first, the compound would bind active molecules forming a homogenous population, and second, the complex, once locked in place would then not be able to contribute to non-specific aggregation. The concentration of the stock protein solution was determined and multiplied by 2.4. This calculation provided the excess inhibitor to be added to the dilute protein sample before the concentration. The appropriate amount of 50 mM inhibitor stock solution (in 100% DMSO) was added, and the solution was incubated on ice for about 30 minutes to about 60 minutes before concentration. A 30K MWCO Ultrafree-4 concentrator (Millipore, Bedford, Mass.) was used with a pretreatment using 2.0 ml of the following solution: 20 mM Hepes (pH 7.8), 20% Glycerol, 5% PEG 8000, 0.1 M NaCl. The sample was spun at 3810 rpm (3000×g) in an SH-3000 rotor in 10 minute increments until desired volume was achieved. The membrane was rinsed with 2×1.0 ml 20 mM Hepes (pH 7.8). The first aliquot of protein:compound mix was added to the concentrator and spun as above until ½ the volume remained. The concentrator was gently inverted to mix protein, and another aliquot was added. The above procedure was repeated until all of the unconcentrated protein:compound mix was in the concentrator. At this point, the sample was gently concentrated until final volume was reached that would give approximately 20 mg/ml concentration. The concentrated sample was used for co-crystallization studies.

Sparse matrix screening using the commercially available Hampton Screen 1 (Hampton Research, Laguna Nigel, Calif.) and Wizard 1 screens (Emerald Biostructures, Bainbridge Island, Wash.) was performed using the hanging drop method. Crystals were obtained in Hampton Screen 1, condition 11 (1.0 M ammonium phosphate and 0.1 M sodium citrate (pH 5.6)). Crystals were lozenge shaped, twinned, and had dimensions of approximately 0.15 mm-0.2 mm×0.1 mm-0.15 mm. The crystals stained positive for protein with Izit dye (Hampton Research, Laguna Nigel, Calif.). No other crystals were obtained from this screen. Initial optimization experiments resulted in crystals that possessed sharp and well-defined edges. Crystals here were still slightly twinned, and of approximately 0.2 mm-0.25 mm×0.1 mm-0.2 mm in size. Further optimization with a focused screen yielded single crystals in trapezoidal morphology, with approximate dimensions of 0.25 mm-0.4 mm×0.15 mm-0.25 mm. The next set of optimization experiments introduced ammonium citrate as a buffer system in the range of pH 4.5-6.1. These solutions, along with careful optimization of ammonium phosphate concentration yielded single crystals in the 0.35 mm×0.2 mm size, which diffracted to 2.5 Å on an X-ray source. The crystals grew in 0.7 M ammonium phosphate and 0.1 M ammonium citrate (pH 4.71). For cryogenic experiments, synthetic mother liquor based on the well solution where the drops crystallized was prepared with a range of DMSO or glycerol. A typical cryo solution was: 0.7 M ammonium phosphate, 0.05 M ammonium citrate (pH 4.71), 0.05 M sodium borate (pH 8.5), and 5-30% glycerol in 5% increments. Attempts to loop out single crystals for soaking experiments resulted in the eventual cracking of the crystal. Experiments where the cryo solution was added to the crystallization drop in a stepwise, incremental fashion over a 3 minute incubation time resulted in crystals soaked into 25% glycerol. The crystal was then flash frozen in liquid nitrogen and held in a storage Dewar until time for data collection on the X-ray source.

X-Ray Diffraction Characterization

Initial data collection was carried out at the Advanced Photon Source (Argonne, Ill.) at beamline 17-ID. These initial crystals were very small, but diffracted to 3.5 Å using synchrotron radiation. Subsequent data collection was carried out on another X-ray source (a Rigaku RUH3R X-ray generator using osmic confocal mirros) with a R-axis IV++ detector (Molecular Structure Corporation, The Woodlands, Tx). Optimized crystals (significantly larger than the initial ones tested at the synchrotron) diffracted to 2.5 Å. Crystals were of the space group $P2_1$, with cell dimensions of a=81±20 Å, b=103±20 Å, c=100±20 Å, $\alpha=\gamma=90°$, and $\beta=105±10°$. The Matthews coefficient for these crystals, assuming that there are three molecules in the asymmetric unit, is 2.7 Å/Da with 54% solvent. The structure determination (see below) revealed the presence of electron density in the active site appropriate for the inhibitor shown in FIG. 1.

Molecular Replacement

A molecular replacement solution was determined using AMORE (Navaza, *Acta Cryst.*, D50:157-63 (1994); Collaborative Computational Project N4, *Acta Cryst*. D50:760-63 (1994))) by utilizing a previously solved structure of human BACE from CHO crystals. The initial rotation solution gave three strong peaks of 11.7σ, 11.1σ, and 10.8σ The presence of the three strong peaks suggested that three molecules might be present in the asymmetric unit. A translation search in space group $P2_1$, resulted in a correlation coefficient of 33.2 with an R-factor of 47.8% to 4 Å resolution for the first molecule. A translation search for the second molecule (keeping the first molecule fixed) resulted in an improved correlation coefficient of 42.8 with an R-factor of 43.6% to 4 Å resolution for both molecules. A translation search for the third molecule (keeping the first two molecules fixed) resulted in an improved correlation coefficient of 63.8 with an R-factor of 35.3% to 4 Å resolution for all three molecules.

TABLE 7

Data collection statistics for initial data set of Human BACE formed from E. coli (pET11a-BACE) produced protein used for the intial molecular replacement solution (data collected at λ 1.0000 Å at APS, 17-ID). Data processed with HKL2000.

| Shell limit | | | | | | | |
|---|---|---|---|---|---|---|---|
| Lower | Upper | Average | Average | | Norm. | Linear | Square |
| Angstrom | | I | error | stat. | Chi**2 | R-fac | R-fac |
| 50.00 | 6.12 | 1967.3 | 130.2 | 117.8 | 0.731 | 0.051 | 0.050 |
| 6.12 | 4.86 | 1310.8 | 187.1 | 183.3 | 0.344 | 0.079 | 0.084 |
| 4.86 | 4.24 | 1629.5 | 237.3 | 232.5 | 0.384 | 0.085 | 0.081 |
| 4.24 | 3.85 | 1015.3 | 264.6 | 262.7 | 0.324 | 0.139 | 0.123 |
| 3.85 | 3.58 | 744.0 | 289.1 | 288.1 | 0.296 | 0.198 | 0.183 |
| 3.58 | 3.37 | 407.7 | 297.4 | 297.1 | 0.253 | 0.328 | 0.290 |
| 3.37 | 3.20 | 256.3 | 300.3 | 300.1 | 0.223 | 0.460 | 0.385 |
| 3.20 | 3.06 | 160.3 | 311.7 | 311.6 | 0.222 | 0.649 | 0.530 |
| 3.06 | 2.94 | 152.7 | 343.0 | 342.9 | 0.232 | 0.689 | 0.537 |
| 2.94 | 2.84 | 293.8 | 318.0 | 317.3 | 0.424 | 0.556 | 0.515 |
| All reflections | | 934.4 | 253.8 | 250.8 | 0.362 | 0.126 | 0.100 |

Model Building and Refinement

Further rigid body refinement of the model in CNX (Molecular Simulations, Inc) followed by minimization refinement gave an R-factor of 28.9% and a Free R-factor of 33.2% to 3.4 Ӏ with an overall B-factor of 33.3 Å$^2$. The subsequent availability of a higher resolution data set to 2.15 Å afforded the opportunity to conduct a suitable refinement of the structure. The refinement against higher resolution data was initiated with a rigid body refinement followed by minimization and B-factor refinement leading to a R-factor of 31.6% and a Free R-factor of 34.8%. During each cycle of refinement a bulk solvent correction was incorporated (Jiang et al., *J. Mol. Biol.*, 243:100-15 (1994)). Progress of the refinement was monitored by a decrease in both the R-factor and Free R-factor.

At this point, inspection of the electron density map within the active site revealed electron density that was unaccounted for by the protein model and consistent with the shape of the inhibitor shown in FIG. 1 that was present in the crystallization conditions. Model building was done using the program CHAIN (Sack, *Journal of Molecular Graphics*, 6:224-25 (1988)) and LORE (Finzel, *Meth. Enzymol.*, 277:230-42 (1997)). Rebuilding of the model and the addition of water molecules into the model using the 2.15 Å resolution map afforded the opportunity for further cycles of refinement (including the inhibitor) giving improvement of the R-factor to 24.5% and a Free R-factor of 27.3%. The model includes three residues from the N terminal pro-region (61P-63P), residues 1-157, 169-309, and 316-385. Loops for residues

TABLE 8

Data collection statistics for 2.15 Å resolution data set of Human BACE formed from E. coli (pET11a-BACE) produced protein used for refinement (data collected at λ 1.54 Å on home source X-rays). Data processed with D*trek.

| Rmerge vs Resolution | | | | | | | | | |
|---|---|---|---|---|---|---|---|---|---|
| Resolution range | Average counts | Num obs | Num rejs | Num ovlps | Num mults | <<I>/<sig>> | ChiSq norm | Rmerge shell | Rmerge cumul |
| 19.92-4.61 | 11176 | 42087 | 465 | 41527 | 8927 | 16.2 | 0.67 | 0.034 | 0.034 |
| 4.61-3.67 | 11419 | 41602 | 267 | 41285 | 8845 | 15.2 | 0.68 | 0.037 | 0.035 |
| 3.67-3.21 | 5995 | 41314 | 334 | 40922 | 8797 | 11.5 | 0.91 | 0.052 | 0.039 |
| 3.21-2.92 | 2952 | 41070 | 399 | 40606 | 8752 | 8.4 | 1.10 | 0.074 | 0.042 |
| 2.92-2.71 | 1601 | 40643 | 545 | 40005 | 8654 | 6.0 | 1.28 | 0.106 | 0.045 |
| 2.71-2.55 | 981 | 40599 | 683 | 39773 | 8615 | 4.4 | 1.31 | 0.142 | 0.048 |
| 2.55-2.42 | 630 | 40344 | 731 | 39480 | 8578 | 3.5 | 1.24 | 0.181 | 0.050 |
| 2.42-2.32 | 430 | 40120 | 685 | 39268 | 8515 | 2.9 | 1.08 | 0.220 | 0.052 |
| 2.32-2.23 | 335 | 39822 | 647 | 39030 | 8481 | 2.5 | 0.97 | 0.255 | 0.054 |
| 2.23-2.15 | 221 | 39729 | 374 | 39249 | 8521 | 2.2 | 0.76 | 0.310 | 0.055 |
| 19.92-2.15 | 3655 | 407330 | 5130 | 401145 | 86685 | 7.4 | 1.00 | 0.055 | 0.055 |

| Redundancy vs Resolution | | | | | | | | | | |
|---|---|---|---|---|---|---|---|---|---|---|
| Resolution | Calc | Percent of reflections measured N times, N = | | | | | | | % Comp | % Comp |
| range | unique | 0 | 1 | 2 | 3 | 4 | 5-8 | 9-12 | >12 | shell | cumul |
| 19.92-4.61 | 9021 | 0.0 | 1.1 | 6.4 | 2.4 | 32.3 | 57.8 | 0.0 | 0.0 | 100.0 | 100.0 |
| 4.61-3.67 | 8896 | 0.0 | 0.6 | 4.7 | 3.4 | 27.2 | 64.1 | 0.0 | 0.0 | 100.0 | 100.0 |
| 3.67-3.21 | 8880 | 0.3 | 0.7 | 4.7 | 4.0 | 25.1 | 65.3 | 0.0 | 0.0 | 99.7 | 99.9 |
| 3.21-2.92 | 8856 | 0.4 | 0.7 | 4.9 | 4.3 | 24.1 | 65.5 | 0.0 | 0.0 | 99.6 | 99.8 |
| 2.92-2.71 | 8817 | 0.8 | 1.1 | 5.2 | 4.6 | 23.4 | 64.9 | 0.0 | 0.0 | 99.2 | 99.7 |
| 2.71-2.55 | 8862 | 1.2 | 1.6 | 5.2 | 4.8 | 22.9 | 64.4 | 0.0 | 0.0 | 98.8 | 99.6 |
| 2.55-2.42 | 8820 | 1.2 | 1.5 | 5.6 | 5.0 | 22.6 | 64.1 | 0.0 | 0.0 | 98.8 | 99.4 |
| 2.42-2.32 | 8822 | 1.6 | 1.9 | 5.3 | 5.0 | 22.7 | 63.6 | 0.0 | 0.0 | 98.4 | 99.3 |
| 2.32-2.23 | 8800 | 2.0 | 1.6 | 5.6 | 5.0 | 22.8 | 63.0 | 0.0 | 0.0 | 98.0 | 99.2 |
| 2.23-2.15 | 8831 | 2.3 | 1.2 | 5.6 | 4.8 | 23.2 | 62.9 | 0.0 | 0.0 | 97.7 | 99.0 |
| 19.92-2.15 | 88605 | 1.0 | 1.2 | 5.3 | 4.3 | 24.6 | 63.5 | 0.0 | 0.0 | 99.0 | 99.0 |

158-168 and 310-316 were disordered in the electron density and therefore have been omitted from the model.

TABLE 9

Refinement Statistics for structure of Human BACE from (pET11a-BACE)

| | R-factor | Free R-factor | No. of reflections |
|---|---|---|---|
| 20-2.15 Å F ≧ 2σ | 0.245 | 0.273 | 87560 |

| | Bonds (Å) | Angles (°) |
|---|---|---|
| r.m.s deviation from ideal geometry | 0.009 | 1.5 |

| | Number of atoms | Average B-factor |
|---|---|---|
| Protein | 8790 | 36.6 |
| Waters | 258 | 35.3 |
| Ligand | 123 | 31.4 |
| Total | 9171 | 36.5 |

Example 2

Crystallization and Structure Determination of Human BACE in C2 Crystal Form

Expression, Purification, and Crystallization

A third BACE construct, pQE70-Met-Arg-Gly-Ser-Phe-Val-Glu- . . . Thr-Asp-Glu-Ser-Arg-Ser-(His)$_6$ (see SEQ ID NO:3) referred to as PQE70-BACE was cloned and expressed as inclusion bodies. Inclusion bodies obtained from 40 liters of cell culture were washed one time in 700 ml of 10 mM TRIS buffer, pH 8.12, 1 mM EDTA (TE). The inclusion bodies were extracted with 400 ml 7.5 M urea, 100 mM AMPSO, 1 mM glycine, 1 mM EDTA, and 100 mM β-Mercaptoethanol (BME), pH 10.5-10.8. After centrifugation, the protein concentration of the supernatant was adjusted by dilution with the above buffer to read ~5.0 at $A_{280}$. The protein was then diluted with 7.5 M urea, 100 mM AMPST, 1 mM glycine, 1 mM EDTA, and the BME concentration adjusted to 10 mM by the addition of BME to read an $A_{280}$~0.5 and a pH=10.5-10.8. The solution was centrifuged. Analysis of the sample in 7.5 M urea by SDS-PAGE revealed BACE as the major component of the solubilized inclusion bodies. BACE migrated as a band of Mr~45,000. Refolding was carried out by a 20-25 fold dilution with cold water (4-15° C.). Upon dilution, the pH dropped automatically to 9.5-10.2. The sample was then allowed to rest in the cold room. Activity assays were performed daily to monitor protein refolding. Results from various experiments indicated that maximal activity was usually reached after 4-5 weeks.

Prior to purification, the pH of the refolded protein was lowered from about 10 to 8.5 with HCl. The solution was loaded onto three 50 ml Q-Sepharose columns (Pharmacia Biotech XK 50). The columns were pre-equilibrated in 0.4 M Urea, 10 mM AMPSO, pH 8.5. After refolded protein was loaded onto the columns, they were washed with 500 ml of 0.4 M Urea, 10 mM TRIS, pH 8.2. The columns were eluted with 180-245 ml of 0.75 M NaCl in 0.4 M Urea 10 mM TRIS buffer, pH 8.2. The eluates were then dialyzed versus 20 mM HEPES, pH 8.0. The samples were then removed from dialysis and dropped into 1 M NaMES, pH 5.7 (0.1 M final concentration). After centrifugation (20K×g) the supernatant was dropped into 1 M Na-acetate, 1 M NaMES, pH 5.0 (0.2 M Na-acetate, 0.28 M Na-MES was the final concentration). No precipitation was observed at this step. This solution was then applied to a 15 ml affinity column equilibrated at the same pH. The column was washed with 6 column volumes of 20 mM sodium acetate buffer pH 4.5, 150 mM NaCl. BACE was eluted at pH 8.5 using about 50 ml of 0.1 M borate buffer. The resin had been cross-linked with the synthetic peptide shown in FIG. 2. This final step removed any residual contaminants. From 40 liter of *E. coli* cell culture, the amount of protein obtained was 137 mg of highly purified pQE70-BACE construct. Purified pQE70-BACE was dialyzed into 100 mM NaBorate pH 8.5.

In an effort to reduce non-specific aggregation, the enzyme was concentrated in the presence of the inhibitor. The purpose of this was two-fold: First, the compound would bind active molecules forming a homogenous population, and second, the complex, once locked in place would then not be able to contribute to non-specific aggregation. The concentration of the stock protein solution was determined and multiplied by 2.4. This calculation provides the excess inhibitor to be added to the dilute protein sample before the concentration. The appropriate amount of 50 mM inhibitor stock solution (in 100% DMSO) was added, and the solution was incubated on ice 30 minutes before concentration. A 30K MWCO (Molecular Weight Cut-Off) Ultrafree-4 concentrator (Millipore, Bedford, Mass.) was pretreated with 2.0 ml of the following solution: 20 mM Hepes pH 7.8, 20% Glycerol, 5% PEG 8000, 0.1 M NaCl. The sample was spun at 3810 rpm (3000×g) in an SH-3000 rotor in 10 minute increments until desired volume is achieved. The membrane was rinsed with 2×1.0 ml 20 mM Hepes pH 7.8. The first aliquot of protein:compound mix was added to the concentrator and spun as above until ½ the volume remained. The concentrator was gently inverted to mix the protein and another aliquot was added. The above procedure was repeated until all of the unconcentrated protein:compound mix was in the concentrator. At this point, the sample was gently concentrated until a final volume was reached that yielded approx. 8-10 mg/ml concentration. This concentrated sample was used for co-crystallization studies. It was also determined that concentrating the protein in the absence of inhibitor to a concentration of 10-13 mg/ml and then subsequently adding inhibitor to the protein provided a protein sample that would crystallize albeit at a slower rate.

Sparse matrix screening of pQE70-BACE in the presence of the inhibitor shown in FIG. 1 at 20° C. in the hanging drop vapor diffusion method was performed with the commercially available Wizard I screen (Emerald Biostructures, Bainbridge Island, Wash.) and Hampton I screen (Hampton Research, Laguna Nigel, Calif.). A shower of microcrystals was observed in Wizard I screen condition 45 (20% PEG 3000 (precipitant), 0.1 M sodium acetate pH 4.5 (buffer)) and Hampton I screen condition 37 (8% PEG 4000 (precipitant), 0.1 M sodium acetate pH 4.6 (buffer)). First round optimization experiments, pQE70-BACE produced crystals in 0.1 M sodium acetate pH 4.5-5.6 (buffer) and PEG 2000, 3000, 4000, and 8000 (precipitants) at 20° C. Initial crystals grown in PEG 3000 consisted of rod clusters and single rod shaped crystals with a large depletion. A crystal grown in 16% PEG 3000 (precipitant) and 0.1 M sodium acetate pH 4.6 (buffer) at 20° C., with an approximate size of 0.6×0.15 mm, diffracted to 1.7 Å at the Argonne National Laboratory. The cryogenic solution for this crystal consisted of synthetic mother liquor based on the well solution and glycerol: 16% PEG 3000, 0.1 M sodium acetate pH 4.6, and 5-30% glycerol (cryoagent) in 5% increments. The cryogenic solutions were added stepwise in 5-minute increments with increasing percentages of glycerol. The crystal was looped out and flash frozen in liquid nitrogen. The crystal contains one molecule per asymmetric unit with cell dimensions of a=73.1 Å, b=105.1 Å, c=50.5 Å, α=90°, β=94.8°, γ=90° in space group C2.

Second round optimization also resulted in large single crystals, with an approximate size of 0.3-0.4×0.12-0.2 mm, in 4-6% PEG 4000 and PEG 8000 (precipitants), 0.1 M sodium acetate pH 4.6-5.6 (buffers) at 20° C. The typical cryogenic solution for these crystals consisted of one percentage higher of the same PEG condition found in the well mother liquor of the crystal, 0.1 M sodium acetate (pH of the mother liquor), and 25% glycerol. The cryogenic solutions were added every 5 minutes with stepwise additions of 0.1 μl, 0.25 μl, 0.50 μl, 1.0 μl, and 2.0 μl. After a one hour soak, crystals were looped out and flash frozen in liquid nitrogen. These crystals have the same unit cell as the pET11a crystals (a=81 Å, b=103 Å, c=100 Å, α=γ=90, β=105°) with a space group of P2$_1$ and three molecules per asymmetric unit but diffracted to lower resolution (2.5-2.8 Å) than the C2 crystal form, discussed above.

Third round optimization revealed that the percentage of PEG (precipitant) was the critical component required to distinguish between the C2 and P2$_1$ crystal forms. The greater the percentage of precipitant present, the more dehydrated the crystals become resulting in higher resolution diffraction (the solvent content in the P2$_1$ crystals is 54% compared to the 42% solvent content for the C2 crystals). Crystallization in 8% PEG or less reproducibly gave the lower resolution P2$_1$ crystal form while crystallization in 16% PEG or more (up to 45% PEG) reproducibly gave the higher resolution C2 crystal form. Alternative PEGs such as PEG 200, PEG 350 MME, PEG 400, PEG 550 MME, PEG 750 MME, PEG 1000, PEG 2000, PEG 2000 MME, PEG 3000, PEG 4000, PEG 8000 also produce suitable crystals when used with pQE70-BACE. The buffer for crystallizing with the different forms of PEG was 0.1 M sodium acetate pH 4.6-5.6 at a temperature of 20° C. No additional salt was required for crystallization. In addition, streak seeding at the stage of setting up the hanging drops aided crystal growth. A range of protein concentration from 2 mg/ml to 13 mg/ml has proven useful in preparing crystals.

X-Ray Diffraction Characterization

Initial data collection was carried out on home source X-rays using a Rigaku RUH3R X-ray generator (with osmic confocal mirros) and a R-axis IV++ detector (Molecular Structure Corporation, The Woodlands, Tex.). Initial analysis of the crystals revealed 1.9 Å diffraction on the home source. The same crystal was refrozen and transported to the synchrotron for subsequent data collection at the Advanced Photon Source (Argonne, Ill.) at beamline 17-ID. Using synchrotron radiation, the crystal diffracted to 1.7 Å resolution. Crystals were of the space group C2 with cell dimensions of a=73.1 Å, b=105.1 Å, c=50.5 Å, α=90°, β=94.8°, γ=90°. The Matthews coefficient for these crystals assuming that there is one molecule in the asymmetric unit is 2.1 Å/Da with 42% solvent. The structure determination (see below) revealed the presence of electron density in the active site appropriate for the inhibitor shown in FIG. 1.

Molecular Replacement

The structure was solved by molecular replacement. A solution was determined using AMORE (Navaza, *Acta Cryst.*, D50:157-63 (1994); Collaborative Computational Project N4, *Acta Cryst.* D50:760-3 (1994)) by utilizing a previously solved structure of human BACE produced in *E. coli* from the pET11a vector. The initial rotation solution gave a single strong peaks of 16.9σ. A translation search in space group C2 resulted in a correlation coefficient of 57.2 with an R-factor of 38.3% to 4 Å resolution. The high correlation coefficient and low R-factor suggested that the entire protein contents of the unit cell had been correctly identified; therefore, the search for additional molecules was abandoned.

TABLE 10

Data collection statistics for 1.9 Å resolution data set of Human BACE derived from *E. coli* pQE70-BACE (C2 crystal form) produced protein used for refinement (data collected at λ 1.54 Å on home source X-rays). Data was processed with D*trek.

| Rmerge vs Resolution | | | | | | | | | |
|---|---|---|---|---|---|---|---|---|---|
| Resolution range | Average counts | Num obs | Num rejs | Num ovlps | Num mults | <<I>/<sig>> | ChiSq norm | Rmerge shell | Rmerge cumul |
| 19.97-4.08 | 33303 | 11727 | 46 | 11666 | 2975 | 10.3 | 0.35 | 0.039 | 0.039 |
| 4.08-3.25 | 27063 | 11593 | 43 | 11536 | 2913 | 9.6 | 0.48 | 0.048 | 0.043 |
| 3.25-2.84 | 11447 | 11354 | 44 | 11298 | 2839 | 8.1 | 0.75 | 0.066 | 0.047 |
| 2.84-2.58 | 6285 | 11441 | 77 | 11343 | 2852 | 6.8 | 0.99 | 0.080 | 0.049 |
| 2.58-2.39 | 4188 | 11239 | 98 | 11112 | 2785 | 5.8 | 1.22 | 0.097 | 0.052 |
| 2.39-2.25 | 3250 | 11130 | 123 | 10975 | 2753 | 5.1 | 1.30 | 0.111 | 0.054 |
| 2.25-2.14 | 2298 | 11102 | 164 | 10893 | 2732 | 4.4 | 1.40 | 0.131 | 0.056 |
| 2.14-2.05 | 1621 | 9532 | 111 | 9355 | 2350 | 3.7 | 1.41 | 0.149 | 0.057 |
| 2.05-1.97 | 1278 | 6190 | 95 | 6012 | 1527 | 3.6 | 1.26 | 0.147 | 0.058 |
| 1.97-1.90 | 798 | 4131 | 47 | 4004 | 1026 | 3.1 | 1.16 | 0.174 | 0.058 |
| 19.97-1.90 | 10512 | 99439 | 848 | 98194 | 24752 | 6.5 | 1.00 | 0.058 | 0.058 |

| Redundancy vs Resolution | | | | | | | | | | |
|---|---|---|---|---|---|---|---|---|---|---|
| Resolution range | Calc unique | Percent of reflections measured N times, N = | | | | | | | % Comp shell | % Comp cumul |
| | | 0 | 1 | 2 | 3 | 4 | 5-8 | 9-12 | >12 | | |
| 19.97-4.08 | 3039 | 1.6 | 0.5 | 5.3 | 0.6 | 88.5 | 3.5 | 0.0 | 0.0 | 98.4 | 98.4 |
| 4.08-3.25 | 3011 | 2.8 | 0.5 | 3.2 | 0.8 | 89.5 | 3.3 | 0.0 | 0.0 | 97.2 | 97.8 |
| 3.25-2.84 | 2964 | 3.8 | 0.4 | 2.4 | 0.6 | 89.3 | 3.5 | 0.0 | 0.0 | 96.2 | 97.3 |
| 2.84-2.58 | 3013 | 4.6 | 0.7 | 2.5 | 0.5 | 88.4 | 3.3 | 0.0 | 0.0 | 95.4 | 96.8 |
| 2.58-2.39 | 2974 | 5.4 | 1.0 | 2.0 | 0.7 | 87.2 | 3.8 | 0.0 | 0.0 | 94.6 | 96.4 |

TABLE 10-continued

Data collection statistics for 1.9 Å resolution data set of Human BACE derived from
E. coli pQE70-BACE (C2 crystal form) produced protein used for refinement (data
collected at λ 1.54 Å on home source X-rays). Data was processed with D*trek.

| | | | | | | | | | | |
|---|---|---|---|---|---|---|---|---|---|---|
| 2.39-2.25 | 2963 | 6.0 | 1.1 | 2.1 | 0.7 | 86.4 | 3.7 | 0.0 | 0.0 | 94.0 | 96.0 |
| 2.25-2.14 | 2974 | 6.6 | 1.5 | 2.1 | 0.7 | 85.4 | 3.7 | 0.0 | 0.0 | 93.4 | 95.6 |
| 2.14-2.05 | 2986 | 19.1 | 2.2 | 1.4 | 1.6 | 72.7 | 2.9 | 0.0 | 0.0 | 80.9 | 93.8 |
| 2.05-1.97 | 2985 | 46.1 | 2.8 | 1.7 | 2.0 | 45.2 | 2.2 | 0.0 | 0.0 | 53.9 | 89.3 |
| 1.97-1.90 | 2978 | 62.9 | 2.7 | 1.2 | 2.2 | 29.9 | 1.2 | 0.0 | 0.0 | 37.1 | 84.1 |
| 19.97-1.90 | 29887 | 15.9 | 1.3 | 2.4 | 1.0 | 76.3 | 3.1 | 0.0 | 0.0 | 84.1 | 84.1 |

| Resolution range | Percent of reflections measured AT LEAST N times, N = | | | | | | |
|---|---|---|---|---|---|---|---|
| | 13 | 9 | 5 | 4 | 3 | 2 | 1 |
| 19.97-1.90 | 0.0 | 0.0 | 3.1 | 79.4 | 80.4 | 82.8 | 84.1 |

TABLE 11

Data collection statistics for 1.7 Å resolution dataset of Human BACE derived from
E. coli pQE70-BACE (C2 crystal form) produced protein used for the intial molecular
replacement solution (data collected at λ 1.0000 Å at APS, 17-ID).
Data was processed with HKL2000.
Summary of reflections intensities and R-factors by shells
R linear = SUM (ABS(I − <I>))/SUM (I)
R square = SUM ((I − <I>)  2)/SUM (I  2)
Chi2 = SUM ((I − <I>)  2)/(Error ** 2 * N/(N − 1)))
In all sums single measurements are excluded

| Shell limit | | Average | Average | | Norm. | Linear | Square |
|---|---|---|---|---|---|---|---|
| Lower | Upper | I | error | stat. | Chi**2 | R-fac | R-fac |
| Angstrom | | | | | | | |
| 50.00 | 3.66 | 37330.4 | 701.7 | 364.7 | 2.455 | 0.039 | 0.045 |
| 3.66 | 2.91 | 18841.1 | 418.8 | 278.7 | 2.645 | 0.054 | 0.059 |
| 2.91 | 2.54 | 7573.0 | 231.6 | 188.0 | 2.262 | 0.069 | 0.074 |
| 2.54 | 2.31 | 4744.8 | 196.2 | 174.2 | 1.911 | 0.085 | 0.088 |
| 2.31 | 2.14 | 3766.7 | 199.8 | 185.1 | 1.655 | 0.097 | 0.099 |
| 2.14 | 2.02 | 2682.2 | 195.6 | 186.9 | 1.324 | 0.115 | 0.110 |
| 2.02 | 1.91 | 1738.0 | 182.7 | 178.3 | 1.079 | 0.143 | 0.131 |
| 1.91 | 1.83 | 1038.1 | 170.3 | 168.2 | 0.833 | 0.183 | 0.159 |
| 1.83 | 1.76 | 665.1 | 166.9 | 165.9 | 0.691 | 0.235 | 0.200 |
| 1.76 | 1.70 | 625.6 | 219.6 | 219.0 | 0.608 | 0.220 | 0.205 |
| All reflections | | 8296.7 | 272.2 | 211.6 | 1.651 | 0.060 | 0.052 |

| Shell | | I/Sigma in resolution shells: | | | | | | | | |
|---|---|---|---|---|---|---|---|---|---|---|
| Lower | Upper | % of reflections with I/Sigma less than | | | | | | | | |
| limit | limit | 0 | 1 | 2 | 3 | 5 | 10 | 20 | >20 | total |
| 50.00 | 3.66 | 0.1 | 0.3 | 0.5 | 0.6 | 0.7 | 1.7 | 4.2 | 93.9 | 98.0 |
| 3.66 | 2.91 | 0.4 | 0.9 | 1.4 | 2.1 | 3.6 | 7.3 | 16.0 | 82.5 | 98.6 |
| 2.91 | 2.54 | 1.0 | 2.4 | 3.8 | 5.4 | 8.0 | 16.1 | 34.0 | 64.0 | 98.0 |
| 2.54 | 2.31 | 1.6 | 3.7 | 6.8 | 9.4 | 15.0 | 27.8 | 51.2 | 46.5 | 97.7 |
| 2.31 | 2.14 | 2.2 | 5.6 | 9.0 | 12.7 | 20.3 | 36.3 | 62.3 | 34.8 | 97.1 |
| 2.14 | 2.02 | 2.3 | 8.1 | 14.3 | 19.6 | 29.6 | 49.6 | 75.4 | 21.3 | 96.7 |
| 2.02 | 1.91 | 4.0 | 12.6 | 20.9 | 28.6 | 42.2 | 63.5 | 84.6 | 11.7 | 96.3 |
| 1.91 | 1.83 | 6.8 | 20.8 | 32.8 | 42.2 | 56.1 | 75.9 | 89.9 | 5.4 | 95.3 |
| 1.83 | 1.76 | 7.6 | 25.7 | 40.6 | 51.6 | 64.0 | 80.2 | 88.7 | 2.0 | 90.6 |
| 1.76 | 1.70 | 5.5 | 19.7 | 33.2 | 43.6 | 54.5 | 64.1 | 67.7 | 0.3 | 68.0 |
| All hkl | | 3.1 | 10.0 | 16.3 | 21.5 | 29.3 | 42.2 | 57.3 | 36.4 | 93.7 |

Model Building and Refinement

Further rigid body refinement of the model in CNX (Molecular Simulations, Inc) followed by minimization refinement gave an R-factor of 37.5% and a Free R-factor of 40.1% to 4.0 Å with an overall B-factor of 25.0 Å$^2$. Minimization and B-factor refinement led to a R-factor of 30.7% and a Free R-factor of 33.4%. The subsequent availability of a higher resolution data set to 1.7 Å afforded the opportunity to continue the high resolution refinement of the structure. The refinement against higher resolution data was initiated with a rigid body refinement followed by minimization and B-factor refinement leading to a R-factor of 29.6% and a Free R-factor of 30.7%. Including a round of simulated annealing refinement (A. T. Brunger, A. Krukowski, J. W. Erickson *Acta Cryst A* 46:585-93, (1990)) and minimization led to an improved R-factor of 26.3% and a Free R-factor of 28.3%. During each cycle of refinement a bulk solvent correction was incorporated (J. S. Jiang & A. T. Brunger, *J. Mol. Biol.* 243:100-15 (1994)). Progress of the refinement was monitored by a decrease in both the R-factor and Free R-factor.

At this point, inspection of the electron density map within the active site revealed electron density that was unaccounted for by the protein model and consistent with the shape of the inhibitor shown in FIG. 1 that was present in the crystallization conditions. Model building was done using the program CHAIN (J. S. Sack, *Journal of Molecular Graphics* 6:224-5 (1988)) and LORE (B. C. Finzel, *Meth. Enzymol.* 277:230-42 (1997)). Rebuilding of the model and the addition of water molecules into the model using the 1.7 Å resolution map afforded the opportunity for further cycles of refinement (including the inhibitor) giving improvement of the R-factor to 20.6% and a Free R-factor of 23.1%. The model includes three residues from the N terminal pro-region (61P-63P), residues 1-157, 165-309, 317-386. Loops for residues 158-164 and 310-316 were disordered in the electron density and therefore have been omitted from the model.

TABLE 12

Refinement Statistics for structure of Human BACE from pQE70 (C2 crystal form).

|  | R-factor | Free R-factor | No. of reflections |
|---|---|---|---|
| 20-1.70 Å F ≧ 2σ | 0.206 | 0.231 | 37857 |

|  | Bonds (Å) | Angles (°) |
|---|---|---|
| r.m.s deviation from ideal geometry | 0.006 | 1.4 |

|  | Number of atoms | Average B-factor |
|---|---|---|
| Protein | 2982 | 24.6 |
| Waters | 370 | 35.5 |
| Ligand | 41 | 18.7 |
| Total | 3393 | 25.8 |

Example 3

Crystallization and Structure Determination of Human BACE in P4$_3$2$_1$2 crystal form Examples of the crystallization and structure determination of human beta secretase in the P43212 crystal form are disclosed in U.S. Provisional Application Ser. No. 60/290,107, filed May 10, 2001 and U.S. patent application Ser. No. 10/143,502, filed on the same day herewith, and entitled "CRYSTALLIZATION AND STRUCTURE DETERMINATION OF BETA SECRETASE AND/OR BETA SECRETASE-LIKE PROTEINS".

Expression, Purification, and Crystallization

Production of Recombinant Human γ-Secretase in CHO-K1 Cells. The coding sequence was engineered to delete the terminal transmembrane and cytoplasmic domain and introduce a C-terminal hexahistidine tag using the polymerase chain reaction. The 5' sense oligonucleotide primer [CGCTTTGGATCCGTGGACAACCTGAGGGGCAA] (SEQ ID NO:6) was designed to incorporate a BamHI site for ease in subcloning and Kozak consensus sequence around the initiator methionine for optimal translation initiation. The 3' antisense primer [CGCTTTGGTACCCTATGACTCATCT-GTCTGTGGAATGTTG] (SEQ ID NO:7) incorporated a hexahistidine tag and translation termination codon just upstream of the predicted transmembrane domain (Ser$^{432}$) and a NotI restriction site for cloning. The PCR was performed on the plasmid template pcDNA3.1hygroAsp2R for 15 cycles [94° C., 30 sec., 65° C., 30 sec., 72° C., 30 sec] using Pwo I polymerase (Roche Biochemicals, Indianapolis, Ind.) as outlined by the manufacturer. The PCR product was digested to completion with BamHI and NotI and ligated into the BamHI and NotI sites of the Baculovirus transfer vector pVL1393 (PharMingen, San Diego, Calif.). A portion of the ligation was used to transform competent *E. coli* DH5α cells and recombinant clones were selected on ampicillin. Individual clones containing the proper cDNA inserts were identified by PCR. Plasmid DNA from clone (pVL1393/Hu_Asp-2LΔTM(His)$_6$) was prepared by alkaline lysis and banding in CsCl. The integrity of the insert was confirmed by complete DNA sequencing. For CHO-K1 cell expression, plasmid pVL1393/Hu_Asp-2LΔTM(His)$_6$ was digested with BamHI and NotI and the resulting fragment subcloned into the mammalian expression vector pcDNA3.1(hygro) as described above to yield pcDNA3.1(hygro)/Hu_Asp-2LΔTM(His)$_6$).

For expression, CHO-K1 cells (50% confluent) were transfected with cationic liposome/pcDNA3.1(hygro)/Hu_Asp-2LΔTM(His)$_6$ complexes in α-MEM medium containing 10% FBS overnight. Selection was performed in the same medium containing 0.5 mg/L hygromycin B for seven days and surviving cells were cloned by limiting dilution. Eight cell lines were screened for soluble β-secretase by Western blot analysis using a polyclonal rabbit antiserum specific for human β-secretase (UP-191). Conditioned medium from each clonal cell line was concentrated by Ni$^+$-NTA (resin available under the trade designation FAST FLOW from Qiagen, Valencia, Calif.) chromatography and the histidine-tagged polypeptide eluted with buffer containing 50 mM imidazole. Aliquots of the latter fraction were displayed on a PVDF membrane and recombinant soluble human β-secretase was visualized using UP-191 antiserum and alkaline phosphatase conjugated goat antirabbit second antibody. Based on these results, clone #4 showed the highest expression level and was used for all subsequent experiments.

Purification of Recombinant Human/Secretase from CHO-K1 Cells. For purification, the medium was concentrated approximately 10-fold using a tangential flow concentrator equip with a 30,000 molecular weight cutoff cartridge. Solid ammonium sulfate was then slowly added with stirring to the concentrate at 4° C. to a final value of 40% saturation (242 g/L). After stirring at 4° C. for 30 minutes, the suspension was clarified by centrifugation (16,000×g, 60 minutes) and the supernatant taken for further analysis. The 40% ammonium sulfate supernatant was adjusted to 80% saturation by slow addition of solid ammonium sulfate with stirring at 4° C. (281 g/L). After stirring for 30 minutes at 4° C., the insoluble material was collected by centrifugation as indicated above and the 40-80% ammonium sulfate pellet taken for further analysis.

The 40-80% ammonium sulfate pellet was dissolved in 25 mM Tris-HCl (pH 8.5)/0.5 M NaCl/10 mM imidazole (1/10 the original volume) and applied to a 12.5 ml column containing Ni$^+$-NTA resin (available under the trade designation FAST FLOW from Qiagen, Valencia, Calif.) previously equilibrated in the same buffer. Following sample application, the column was washed with 10 column volumes of loading buffer and then eluted with 25 mM Tris-HCl (pH 8.5)/0.5 M NaCl/50 mM imidazole. The material eluting in 50 mM imidazole was pooled, concentrated approximately 10-fold using a YM 30 membrane (30,000 MWCO), and then dialyzed against 10 mM HEPES-Na (pH 8.0) using 50,000 molecular weight cutoff tubing. For affinity purification, the synthetic peptide Ser-Glu-Val-Asn-Sta-Val-Ala-Glu-Phe-Arg-Gly-Gly-Cys (where Sta—statine) (FIG. 2, SEQ ID NO:4) was synthesized and coupled to SULFO-LINK® resin (Pierce Chemical Company, Rockford, Ill.) as recommended by the manufacture. The dialyzed material from above was adjusted to 0.1 M NaOAc (pH 4.5) by addition of 1/10 volume of 1.0 M NaOAc (pH 4.5) and immediately applied to the synthetic peptide shown in FIG. 2/SULFO-LINK® column (6 ml containing 1.0 mg of the synthetic peptide shown in FIG. 2/ml of resin) that had been previously equilibrated in 25 mM NaOAc (pH 4.5). Following sample application, the column was washed with 10 column volumes of 25 mM NaOAc (pH 4.5) and then eluted with 50 mM sodium borate (pH 8.5). N-terminal sequence analysis of the affinity purified material revealed an equimolar mixture of pro- and processed human β-secretase beginning at $Thr^1$ and $Glu^{25}$, respectively. The final protein concentration was determined by amino acid analysis assuming a 52 kDa glycoprotein for insect cells and a 60 kDa glycoprotein for CHO cells, respectively.

Cleavage of Beta Secretase by HIV Protease. HIV-1 protease is able to cleave beta secretase at $F^{39}$—$V^{40}$ bond as shown in FIG. 11. It was reasoned that a homogeneous preparation of beta secretase with $V^{40}$ as an N-terminus could be made if conditions could be found to bring the cleavage to completion. The optimal conditions for cleavage were determined by examining the N-terminal sequence of beta secretase after incubation with HIV-1 protease in various conditions. These included a pH range of 4-7, urea concentrations of 0.5-3.0 M, and time increments of 15 minutes, up to 2 hours incubation at 37° C. It was found that at pH 5.7, 0.5 M urea, with 5% HIV protease and 1 hour incubation at 37° C., nearly 100% cleavage of the $F^{39}$—$V^{40}$ bond occurred. The processed enzyme was separated from the other components of the reaction mixture by using an affinity column based on the synthetic peptide shown in FIG. 2 and dialysis. Beta secretase produced by the technique described above is about 10-20% more active than unprocessed beta secretase.

In a typical experiment, 25 mg ($3.85 \times 10^{-7}$ moles) of CHO cell derived beta secretase in 4.65 ml (at 5.38 mg/ml per amino acid analysis) was treated with a 10% molar equivalent of the HIV-1 protease dimer ($3.85 \times 10^{-8}$ moles, $7.69 \times 10^{-4}$ g) in the presence of 0.5 M urea and 0.2 M MES (pH 5.7). Before adding the HIV-1 protease, the beta secretase was prepared in the following manner: 1) 4.65 ml of beta secretase was added to 1.163 ml of 1M MES (pH 5.7) with no precipitate being observed; 2) 0.55 ml of 6 M urea was added to the mixture in step 1 while stirring with some precipitate being observed; 3) 0.222 ml of HIV-1 protease ($\times 3.47$ mg/ml=$7.70 \times 10^{-4}$ g). The mixture was then incubated for 2 hours at 37° C.

Further purification after HIV protease treatment. Afterwards, the mixture was dialyzed overnight versus 0.5 M urea and 0.2 M MES (pH 5.7) at 4° C. using a membrane available under the trade designation SPECTRA/POR 6® Membrane, MWCO: 50,000 (Part No. 132-544) from Spectrum Laboratories (Rancho Dominguez, Calif.). The next morning, the sample was changed into a solution containing 10 mM MES (pH 5.7) and 50 mM NaCl (no urea) at 4° C., and allowed to continue dialyzing for an additional 8 hours. At this point, the solution was spun to remove the precipitate, and the supernatant analyzed by absorbance at 280 nm. It was estimated, using a conversion factor of 0.685 mg/mg AU, that approximately 20.4 mg of material was present to carry forward to the next, and final stage of purification. 20.4 mg of beta secretase in 9.3 ml (containing 10 mM MES (pH 5.7) and 50 mM NaCl (no urea) at 4° C.) from the preceding steps were added to 2.325 ml of 1 M sodium acetate (pH 4.5). It was then applied to a 2 ml affinity column that had been pre-equilibrated with 0.2 M sodium acetate (pH 4.5). The affinity column was made by coupling the synthetic peptide shown in FIG. 2 (1 mg/ml of resin) to 2 ml of a resin available under the trade designation SULFO-LINK® from Pierce Chemical Co. ((Rockford, Ill.). The flow through material was recirculated 2× before washing the column with 20 mM solution (pH 4.5) and 150 mM NaCl. The beta secretase was eluted into 6 ml of 0.1 M sodium borate (pH 8.5). Absorbance at 280 nm indicated a total of 13.6 mg of beta secretase. The affinity column was re-equilibrated, and the process repeated using the flow through. Another 6 ml containing a total of 5.1 mg was recovered (according to absorbance at 280 nm). Thus a combined total of 18.7 mg was realized after treatment of the CHO cell derived beta secretase with HIV-1 protease, and subsequent purification. Thus, a combined total of 18.7 mg was realized after treatment of the CHO cell derived beta secretase with HIV-1 protease, and subsequent purification.

Purified HIV-1 protease treated (and non-treated) beta secretase were assayed for activity b HPLC analysis of the products. Purified HIV-1 protease treated beta secretase showed 10-20% more enzymatic activity than non-treated beta secretase.

Crystallization. The crystallization conditions for HIV protease treated CHO produced beta secretase were found by trying to reproduce untreated CHO cell beta secretase crystallization conditions. The untreated form of the protein contains a 50:50 mixture of pro and processed forms. A tray was set up to attempt to reproduce the crystallization conditions along with test crystallization conditions that were cryogenic. The tray had a row that was 20-25% PEG 2000 MME, 100 mM sodium acetate (pH 4.5), a 0.75 microliter+0.75 microliter reservoir+protein drop, with a 500 microliter reservoir volume in a crystallization plate and an incubation temperature of 20° C. The other three rows were the same as the first with the addition of 10% DMSO for the second row, 10% ethylene glycol for the third row, and 10% glycerol for the fourth row. The tray was streak seeded by using a cat whisker and a seed stock from untreated CHO crystals. Within a week crystals were observed in the second, third, and fourth rows. After three weeks, small crystals were observed in the first row. Later experiments demonstrated that seeding was not necessary. The crystals observed without seeding were of the same form as crystals formed from seeding. Crystals obtained from seeding experiments were of a different crystal form than the original untreated CHO crystals used for seeds.

Detailed Crystallization Method. The protein was obtained in 20 mM HEPES (pH 8.0) and 50 mM NaCl at approximately 1 mg/ml for crystallization studies. During concentration to approximately 25 mg/ml the protein was exchanged into 20 mM HEPES (NaOH, pH 7.75) and the NaCl concentration was diluted to less than 1 mM.

Crystals were grown from the following conditions: protein+compound preparation–20 mg/ml protein, 2 mM of the inhibitor shown in FIG. 1 (dissolved in 100% DMSO), 10% DMSO (including DMSO from compound); well solution: 17-28% PEG 2000 MME or PEG 5000 MME, 50-200 mM sodium acetate (pH 4.5), 0-20% glycerol or 10% ethylene glycol or 10% DMSO or 10% MPD.

Crystallization method: 500 microliters reservoir volume in a hanging drop vapor diffusion tray (plates available under the trade designation VDX plate and CRYSCHEM® plate from Hampton Research, Laguna Niguel, Calif.). The protein and reservoir solutions were added together in a 1:1 ratio on the coverslip or sitting drop post. Drop size of 0.75 microliter+0.75 microliter was preferred, although 0.75-1.5 microliters well+1.5-2 microliters protein was also sufficient to produce crystals. The trays were then stored in a 20° C. incubator for the nucleation and growth phases. Crystals appeared in 7-10 days (with the inhibitor shown in FIG. 1) with final size of 0.3 mm×0.3mm occurring by day 21.

Cryo conditions: With optimal crystallization conditions, the drop was cryogenic (did not form crystalline ice). Reservoir: 20% PEG 2000 MME, 100 mM sodium acetate (pH 4.5), and 10% glycerol. Protein preparation: 20 mg/ml protein, 2 mM of the inhibitor shown in FIG. 1, and 10% DMSO. Crystals that were frozen directly from the crystallization drop did not diffract as well as a crystal mounted in a capillary tube. The diffraction limit of the frozen crystal was 6 Å while a crystal of similar size (0.2 mm×0.2 mm) diffracted to better than 4 Å when mounted in a capillary tube. Optimization of cryo conditions included adding supplemental amounts of a cryo agent to the crystallization drop. The preferred cryo agent was ethylene glycol, however glycerol or DMSO also provided cryoprotection. The method for adding supplemental cryo agent to the drop was as follows: 1 microliter 100% cryo agent was added to 3 microliters of reservoir solution to give a 25% cryo stock; the mixture was allowed to set for 1 minute before 0.5 microliter of the mix was added to a 0.75 microliter+0.75 microliter crystallization drop; after waiting an additional 3 minutes, another 1 microliter of the mixture was added. The second addition of the cryo mix brought the cryo concentration to 12.5%. Cryopreservation was completed by looping out the crystal after about 3 minutes to 2 hours and freezing the crystal by plunging the loop into liquid nitrogen.

X-Ray Diffraction Characterization

All data collection was carried out at the Advanced Photon Source (Argonne, Ill.) at beamline 17-ID. The crystals diffracted to 2.9 Å using synchrotron radiation. Crystals were of the space group $P4_32_12$ with cell constants a=114.0±20 Å, b=114±20 Å, c=190±20 Å, and α=γ=90°. The Matthews coefficient for these crystals assuming that there are two molecules in the asymmetric unit is 2.4 Å/Da with 48% solvent. The structure determination (see below) revealed the presence of electron density in the active site appropriate for the inhibitor shown in FIG. 1.

Molecular Replacement

A molecular replacement solution was determined using AMORE (Navaza, *Acta Cryst.*, D50:157-63 (1994); Collaborative Computational Project N4, *Acta Cryst.* D50:760-63 (1994)) by utilizing a previously solved structure of human beta secretase from CHO crystals. The initial rotation solution gave a single strong peak of 7.8σ with the next strongest peak appearing at 6.8σ and the third strongest peak appearing at 4.0σ. The presence of two strong peaks suggested that two molecules might be present in the asymmetric unit. The final determination of the space group ($P4_12_12$ or $P4_32_12$) was determined experimentally by testing translation searches in each space group. A translation search in the correct space group, $P4_32_12$, resulted in a correlation coefficient of 41.7 with an R-factor of 46.3% to 4 Å resolution for the first molecule. A translation search for the second molecule resulted in an improved correlation coefficient of 60.9 with an R-factor of 38.0 to 4 Å resolution for both molecules.

TABLE 13

Data collection statistics for structure of Human Beta Secretase (data collected at λ 1.0000 Å at APS, 17-ID)

| Shell limit | | Average | Average | | Norm. | Linear | Square |
|---|---|---|---|---|---|---|---|
| Lower | Upper | | | | | | |
| Angstrom | | I | error | stat. | Chi**2 | R-fac | R-fac |
| 20.00 | 5.98 | 6592.1 | 110.7 | 86.2 | 2.032 | 0.044 | 0.047 |
| 5.98 | 4.77 | 3833.6 | 60.8 | 49.6 | 2.020 | 0.060 | 0.065 |
| 4.77 | 4.17 | 3918.4 | 70.5 | 60.1 | 1.933 | 0.067 | 0.074 |
| 4.17 | 3.79 | 2396.6 | 57.0 | 51.5 | 1.377 | 0.078 | 0.079 |
| 3.79 | 3.52 | 1453.6 | 52.5 | 49.9 | 0.869 | 0.094 | 0.094 |
| 3.52 | 3.32 | 853.1 | 51.3 | 50.1 | 0.505 | 0.121 | 0.114 |
| 3.32 | 3.15 | 477.4 | 49.6 | 49.2 | 0.320 | 0.169 | 0.160 |
| 3.15 | 3.02 | 296.8 | 48.9 | 48.7 | 0.232 | 0.234 | 0.215 |

TABLE 13-continued

Data collection statistics for structure of Human Beta Secretase (data collected at λ 1.0000 Å at APS, 17-ID)

| Shell limit | | Average | Average | | Norm. | Linear | Square |
|---|---|---|---|---|---|---|---|
| Lower | Upper | | | | | | |
| Angstrom | | I | error | stat. | Chi**2 | R-fac | R-fac |
| 3.02 | 2.90 | 178.4 | 52.9 | 52.8 | 0.198 | 0.358 | 0.343 |
| 2.90 | 2.80 | 153.4 | 86.7 | 86.7 | 0.277 | 0.442 | 0.474 |
| All reflections | | 2130.2 | 63.7 | 57.7 | 1.089 | 0.071 | 0.062 |

Model Building and Refinement

Further rigid body refinement of the model in CNX (Molecular Simulations, Inc) followed by minimization and group b-factor refinement gave an R-factor of 30.9% and a Free R-factor of 35.6% to 2.9 Å. During each cycle of refinement a bulk solvent correction was incorporated (Jiang et al., *J. Mol. Biol.* 243:100-15 (1994)). Progress of the refinement was monitored by a decrease in both the R-factor and Free R-factor.

At this point, inspection of the electron density map within the active site revealed electron density that was unaccounted for by the protein model and consistent with the shape of the inhibitor shown in FIG. 1 that was present in the crystallization conditions. Model building was done using the program CHAIN (Sack, *Journal of Molecular Graphics*, 6:224-25 (1988)) and LORE (Finzel, *Meth. Enzymol.*, 277:230-42 (1997)). Modest rebuilding of the model into the 2.9 Å resolution map afforded the opportunity for further cycles of refinement (including the inhibitor) giving marginal improvement of the R-factor to 30.7% and a Free R-factor of 36.0%. Residues 158-170 and 311 to 316 were disordered in the electron density and therefore have been omitted from the model.

TABLE 14

Refinement Statistics for structure of Human Beta Secretase

| | R-factor | Free R-factor | No. of reflections |
|---|---|---|---|
| 20-2.9 Å F ≧ 2σ | 0.307 | 0.3600 | 27670 |

| | Bonds (Å) | Angles (°) |
|---|---|---|
| r.m.s deviation from ideal geometry | 0.012 | 1.8 |

| | Number of atoms | Average B-factor |
|---|---|---|
| Protein | 5768 | 74.3 |
| Ligand | 82 | 18.7 |
| Total | 5850 | 73.5 |

The complete disclosure of all patents, patent applications including provisional applications, and publications, and electronically available material (e.g., GenBank amino acid and nucleotide sequence submissions; and protein data bank (pdb) submissions) cited herein are incorporated by reference. The foregoing detailed description and examples have been given for clarity of understanding only. No unnecessary limitations are to be understood therefrom. The invention is not limited to the exact details shown and described; many variations will be apparent to one skilled in the art and are intended to be included within the invention defined by the claims.

| SEQUENCE LISTING FREE TEXT | |
|---|---|
| SEQ ID NO:1 | residues for the *E. coli* expressed recombinant human BACE produced from the pET11a construct |
| SEQ ID NO:2 | residues for the *E. coli* expressed recombinant human BACE produced from the pQE80L construct |
| SEQ ID NO:3 | residues for the *E. coli* expressed recombinant human BACE produced from the pQE70 construct |
| SEQ ID NO:4 | synthetic peptide |
| SEQ ID NO:5 | residues for CHO cell expressed recombinant human beta secretase proteolytically cleaved with HIV protease (used for crystallization) |
| SEQ ID NO:6 | 5' sense oligonucleotide primer |
| SEQ ID NO:7 | 3' antisense oligonucleotide primer |

What is claimed is:

1. A method of using an isolated crystal of beta secretase (BACE) of SEQ ID NO:3 having space group symmetry C2, unit cell dimensions of a, b, and c, wherein a is about 53 Å to about 93 Å, b is about 85 Å to about 125 Å, and c is about 40 Å to about 60 Å; $\alpha=\gamma=90°$, $\beta$ is about 85° to about 105°;
   selecting a potential modifier by performing rational drug design with a three-dimensional structure determined for the crystal, wherein selecting is performed in conjunction with computer modeling;
   adding the potential modifier to a binding assay; and
   detecting a measure of binding, wherein the potential modifier that binds is selected as a potential drug.

2. A method of using an isolated co-crystal of beta secretase (BACE) of SEQ ID NO:3 having space group symmetry C2, unit cell dimensions of a, b, and c, wherein a is about 53 Å to about 93 Å, b is about 85 Å to about 125 Å, and c is about 40 Å to about 60 Å; $\alpha=\gamma=90°$, $\beta$ is about 85° to about 105°;
   selecting a potential modifier by performing rational drug design with a three-dimensional structure determined for the crystal, wherein selecting is performed in conjunction with computer modeling;
   adding the potential modifier to a binding assay; and
   detecting a measure of binding, wherein the potential modifier that binds is selected as a potential drug.

3. The method of claim 2 wherein the exposing comprises soaking.

4. The method of claim 2 wherein the samples include a variety of different functional groups.

5. The method of claim 3, wherein the crystal of BACE wherein a is 73.1 Å, b=105.1 Å, c=50.5 Å, $\alpha=\gamma=90°$, and $\beta=94.8°$.

6. The method of claim 2 further comprising identifying the ligand that forms the ligand-BACE molecular complex.

7. The method of claim 6 wherein one of the determining and identifying comprises collecting x-ray diffraction data.

8. The method of claim 7 wherein one of the determining and identifying comprises calculating an electron density function.

9. A method of using an isolated crystal of beta secretase (BACE) of SEQ ID NO:1 or SEQ ID NO:2 having space group symmetry P21, unit cell dimensions of a, b, and c, wherein a is about 61 Å to about 101 Å, b is about 83 Å to about 123 Å, and c is about 80 Å to about 120 Å; $\alpha=\gamma=90°$, $\beta$ is about 95° to about 115°;
   selecting a potential modifier by performing rational drug design with a three-dimensional structure determined for the crystal, wherein selecting is performed in conjunction with computer modeling;
   adding the potential modifier to a binding assay; and
   detecting a measure of binding, wherein the potential modifier that binds is selected as a potential drug.

10. A method of using an isolated co-crystal of beta secretase (BACE) of SEQ ID NO:1 or SEQ ID NO:2 having space group symmetry $P2_1$, unit cell dimensions of a, b, and c, wherein a is about 61 Å to about 101 Å, b is about 83 Å to about 123 Å, and c is about 80 Å to about 120 A; $\alpha=\gamma=90°$, $\beta$ is about 95° to about 115°;
   selecting a potential modifier by performing rational drug design with a three-dimensional structure determined for the crystal, wherein selecting is performed in conjunction with computer modeling; adding the potential modifier to a binding assay; and
   detecting a measure of binding, wherein the potential modifier that binds is selected as a potential drug.

11. The method of claim 10 wherein the exposing comprises soaking.

12. The method of claim 11 wherein the samples include a variety of different functional groups.

13. The method of claim 10 further comprising identifying the ligand that forms the ligand-BACE molecular complex.

14. The method of claim 13 wherein one of the determining and identifying comprises collecting x-ray diffraction data.

15. The method of claim 13 wherein one of the determining and identifying comprises calculating an electron density function.

* * * * *

SEQUENCE LISTING

<160> NUMBER OF SEQ ID NOS: 7

<210> SEQ ID NO 1
<211> LENGTH: 455
<212> TYPE: PRT
<213> ORGANISM: Homo sapiens

<400> SEQUENCE: 1

```
Met Ala Ser Met Thr Gly Gly Gln Gln Met Gly Arg Gly Ser Met Ala
1               5                   10                  15

Gly Val Leu Pro Ala His Gly Thr Gln His Gly Ile Arg Leu Pro Leu
            20                  25                  30

Arg Ser Gly Leu Gly Gly Ala Pro Leu Gly Leu Arg Leu Pro Arg Glu
        35                  40                  45

Thr Asp Glu Glu Pro Glu Glu Pro Gly Arg Arg Gly Ser Phe Val Glu
50                  55                  60

Met Val Asp Asn Leu Arg Gly Lys Ser Gly Gln Gly Tyr Tyr Val Glu
65                  70                  75                  80

Met Thr Val Gly Ser Pro Pro Gln Thr Leu Asn Ile Leu Val Asp Thr
                85                  90                  95

Gly Ser Ser Asn Phe Ala Val Gly Ala Ala Pro His Pro Phe Leu His
            100                 105                 110

Arg Tyr Tyr Gln Arg Gln Leu Ser Ser Thr Tyr Arg Asp Leu Arg Lys
        115                 120                 125

Gly Val Tyr Val Pro Tyr Thr Gln Gly Lys Trp Glu Gly Glu Leu Gly
    130                 135                 140

Thr Asp Leu Val Ser Ile Pro His Gly Pro Asn Val Thr Val Arg Ala
145                 150                 155                 160

Asn Ile Ala Ala Ile Thr Glu Ser Asp Lys Phe Phe Ile Asn Gly Ser
                165                 170                 175

Asn Trp Glu Gly Ile Leu Gly Leu Ala Tyr Ala Glu Ile Ala Arg Pro
            180                 185                 190

Asp Asp Ser Leu Glu Pro Phe Phe Asp Ser Leu Val Lys Gln Thr His
        195                 200                 205

Val Pro Asn Leu Phe Ser Leu Gln Leu Cys Gly Ala Gly Phe Pro Leu
    210                 215                 220

Asn Gln Ser Glu Val Leu Ala Ser Val Gly Gly Ser Met Ile Ile Gly
225                 230                 235                 240

Gly Ile Asp His Ser Leu Tyr Thr Gly Ser Leu Trp Tyr Thr Pro Ile
                245                 250                 255

Arg Arg Glu Trp Tyr Tyr Glu Val Ile Ile Val Arg Val Glu Ile Asn
            260                 265                 270
```

```
Gly Gln Asp Leu Lys Met Asp Cys Lys Glu Tyr Asn Tyr Asp Lys Ser
            275                 280                 285

Ile Val Asp Ser Gly Thr Thr Asn Leu Arg Leu Pro Lys Lys Val Phe
        290                 295                 300

Glu Ala Ala Val Lys Ser Ile Lys Ala Ala Ser Ser Thr Glu Lys Phe
305                 310                 315                 320

Pro Asp Gly Phe Trp Leu Gly Glu Gln Leu Val Cys Trp Gln Ala Gly
                325                 330                 335

Thr Thr Pro Trp Asn Ile Phe Pro Val Ile Ser Leu Tyr Leu Met Gly
            340                 345                 350

Glu Val Thr Asn Gln Ser Phe Arg Ile Thr Ile Leu Pro Gln Gln Tyr
        355                 360                 365

Leu Arg Pro Val Glu Asp Val Ala Thr Ser Gln Asp Asp Cys Tyr Lys
    370                 375                 380

Phe Ala Ile Ser Gln Ser Ser Thr Gly Thr Val Met Gly Ala Val Ile
385                 390                 395                 400

Met Glu Gly Phe Tyr Val Val Phe Asp Arg Ala Arg Lys Arg Ile Gly
                405                 410                 415

Phe Ala Val Ser Ala Cys His Val His Asp Glu Phe Arg Thr Ala Ala
            420                 425                 430

Val Glu Gly Pro Phe Val Thr Leu Asp Met Glu Asp Cys Gly Tyr Asn
        435                 440                 445

Ile Pro Gln Thr Asp Glu Ser
    450                 455

<210> SEQ ID NO 2
<211> LENGTH: 448
<212> TYPE: PRT
<213> ORGANISM: Homo sapiens

<400> SEQUENCE: 2

Met Arg Gly Ser His His His His His His Gly Ser Ile Glu Thr Asp
1               5                   10                  15

Thr Gln His Gly Ile Arg Leu Pro Leu Arg Ser Gly Leu Gly Gly Ala
            20                  25                  30

Pro Leu Gly Leu Arg Leu Pro Arg Glu Thr Asp Glu Glu Pro Glu Glu
        35                  40                  45

Pro Gly Arg Arg Gly Ser Phe Val Glu Met Val Asp Asn Leu Arg Gly
    50                  55                  60

Lys Ser Gly Gln Gly Tyr Tyr Val Glu Met Thr Val Gly Ser Pro Pro
65                  70                  75                  80

Gln Thr Leu Asn Ile Leu Val Asp Thr Gly Ser Ser Asn Phe Ala Val
                85                  90                  95

Gly Ala Ala Pro His Pro Phe Leu His Arg Tyr Tyr Gln Arg Gln Leu
            100                 105                 110

Ser Ser Thr Tyr Arg Asp Leu Arg Lys Gly Val Tyr Val Pro Tyr Thr
        115                 120                 125

Gln Gly Lys Trp Glu Gly Glu Leu Gly Thr Asp Leu Val Ser Ile Pro
    130                 135                 140

His Gly Pro Asn Val Thr Val Arg Ala Asn Ile Ala Ala Ile Thr Glu
145                 150                 155                 160

Ser Asp Lys Phe Phe Ile Asn Gly Ser Asn Trp Glu Gly Ile Leu Gly
                165                 170                 175

Leu Ala Tyr Ala Glu Ile Ala Arg Pro Asp Asp Ser Leu Glu Pro Phe
```

-continued

```
            180                 185                 190
Phe Asp Ser Leu Val Lys Gln Thr His Val Pro Asn Leu Phe Ser Leu
            195                 200                 205
Gln Leu Cys Gly Ala Gly Phe Pro Leu Asn Gln Ser Glu Val Leu Ala
        210                 215                 220
Ser Val Gly Gly Ser Met Ile Ile Gly Gly Ile Asp His Ser Leu Tyr
225                 230                 235                 240
Thr Gly Ser Leu Trp Tyr Thr Pro Ile Arg Arg Glu Trp Tyr Tyr Glu
                245                 250                 255
Val Ile Ile Val Arg Val Glu Ile Asn Gly Gln Asp Leu Lys Met Asp
            260                 265                 270
Cys Lys Glu Tyr Asn Tyr Asp Lys Ser Ile Val Asp Ser Gly Thr Thr
        275                 280                 285
Asn Leu Arg Leu Pro Lys Lys Val Phe Glu Ala Ala Val Lys Ser Ile
    290                 295                 300
Lys Ala Ala Ser Ser Thr Glu Lys Phe Pro Asp Gly Phe Trp Leu Gly
305                 310                 315                 320
Glu Gln Leu Val Cys Trp Gln Ala Gly Thr Thr Pro Trp Asn Ile Phe
                325                 330                 335
Pro Val Ile Ser Leu Tyr Leu Met Gly Glu Val Thr Asn Gln Ser Phe
            340                 345                 350
Arg Ile Thr Ile Leu Pro Gln Gln Tyr Leu Arg Pro Val Glu Asp Val
        355                 360                 365
Ala Thr Ser Gln Asp Asp Cys Tyr Lys Phe Ala Ile Ser Gln Ser Ser
    370                 375                 380
Thr Gly Thr Val Met Gly Ala Val Ile Met Glu Gly Phe Tyr Val Val
385                 390                 395                 400
Phe Asp Arg Ala Arg Lys Arg Ile Gly Phe Ala Val Ser Ala Cys His
                405                 410                 415
Val His Asp Glu Phe Arg Thr Ala Ala Val Glu Gly Pro Phe Val Thr
            420                 425                 430
Leu Asp Met Glu Asp Cys Gly Tyr Asn Ile Pro Gln Thr Asp Glu Ser
        435                 440                 445

<210> SEQ ID NO 3
<211> LENGTH: 406
<212> TYPE: PRT
<213> ORGANISM: Homo sapiens

<400> SEQUENCE: 3

Met Arg Gly Ser Phe Val Glu Met Val Asp Asn Leu Arg Gly Lys Ser
1               5                   10                  15
Gly Gln Gly Tyr Tyr Val Glu Met Thr Val Gly Ser Pro Pro Gln Thr
            20                  25                  30
Leu Asn Ile Leu Val Asp Thr Gly Ser Ser Asn Phe Ala Val Gly Ala
        35                  40                  45
Ala Pro His Pro Phe Leu His Arg Tyr Tyr Gln Arg Gln Leu Ser Ser
    50                  55                  60
Thr Tyr Arg Asp Leu Arg Lys Gly Val Tyr Val Pro Tyr Thr Gln Gly
65                  70                  75                  80
Lys Trp Glu Gly Glu Leu Gly Thr Asp Leu Val Ser Ile Pro His Gly
                85                  90                  95
Pro Asn Val Thr Val Arg Ala Asn Ile Ala Ala Ile Thr Glu Ser Asp
            100                 105                 110
```

-continued

```
Lys Phe Phe Ile Asn Gly Ser Asn Trp Glu Gly Ile Leu Gly Leu Ala
        115                 120                 125

Tyr Ala Glu Ile Ala Arg Pro Asp Asp Ser Leu Glu Pro Phe Phe Asp
130                 135                 140

Ser Leu Val Lys Gln Thr His Val Pro Asn Leu Phe Ser Leu Gln Leu
145                 150                 155                 160

Cys Gly Ala Gly Phe Pro Leu Asn Gln Ser Glu Val Leu Ala Ser Val
                165                 170                 175

Gly Gly Ser Met Ile Ile Gly Ile Asp His Ser Leu Tyr Thr Gly
                180                 185                 190

Ser Leu Trp Tyr Thr Pro Ile Arg Arg Glu Trp Tyr Glu Val Ile
        195                 200                 205

Ile Val Arg Val Glu Ile Asn Gly Gln Asp Leu Lys Met Asp Cys Lys
        210                 215                 220

Glu Tyr Asn Tyr Asp Lys Ser Ile Val Asp Ser Gly Thr Thr Asn Leu
225                 230                 235                 240

Arg Leu Pro Lys Lys Val Phe Glu Ala Ala Val Lys Ser Ile Lys Ala
                245                 250                 255

Ala Ser Ser Thr Glu Lys Phe Pro Asp Gly Phe Trp Leu Gly Glu Gln
                260                 265                 270

Leu Val Cys Trp Gln Ala Gly Thr Thr Pro Trp Asn Ile Phe Pro Val
        275                 280                 285

Ile Ser Leu Tyr Leu Met Gly Glu Val Thr Asn Gln Ser Phe Arg Ile
        290                 295                 300

Thr Ile Leu Pro Gln Gln Tyr Leu Arg Pro Val Glu Asp Val Ala Thr
305                 310                 315                 320

Ser Gln Asp Asp Cys Tyr Lys Phe Ala Ile Ser Gln Ser Ser Thr Gly
                325                 330                 335

Thr Val Met Gly Ala Val Ile Met Glu Gly Phe Tyr Val Val Phe Asp
                340                 345                 350

Arg Ala Arg Lys Arg Ile Gly Phe Ala Val Ser Ala Cys His Val His
                355                 360                 365

Asp Glu Phe Arg Thr Ala Ala Val Glu Gly Pro Phe Val Thr Leu Asp
        370                 375                 380

Met Glu Asp Cys Gly Tyr Asn Ile Pro Gln Thr Asp Glu Ser Arg Ser
385                 390                 395                 400

His His His His His His
                405
```

<210> SEQ ID NO 4
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: protein3
<222> LOCATION: (5)..(5)
<223> OTHER INFORMATION: statine

<400> SEQUENCE: 4

```
Ser Glu Val Asn Xaa Val Ala Glu Phe Arg Gly Gly Cys
1               5                   10
```

<210> SEQ ID NO 5
<211> LENGTH: 399
<212> TYPE: PRT
<213> ORGANISM: Homo sapiens

<400> SEQUENCE: 5

```
Val Glu Met Val Asp Asn Leu Arg Gly Lys Ser Gly Gln Gly Tyr Tyr
1               5                   10                  15
Val Glu Met Thr Val Gly Ser Pro Pro Gln Thr Leu Asn Ile Leu Val
            20                  25                  30
Asp Thr Gly Ser Ser Asn Phe Ala Val Gly Ala Ala Pro His Pro Phe
        35                  40                  45
Leu His Arg Tyr Tyr Gln Arg Gln Leu Ser Ser Thr Tyr Arg Asp Leu
    50                  55                  60
Arg Lys Gly Val Tyr Val Pro Tyr Thr Gln Gly Lys Trp Glu Gly Glu
65                  70                  75                  80
Leu Gly Thr Asp Leu Val Ser Ile Pro His Gly Pro Asn Val Thr Val
                85                  90                  95
Arg Ala Asn Ile Ala Ala Ile Thr Glu Ser Asp Lys Phe Phe Ile Asn
            100                 105                 110
Gly Ser Asn Trp Glu Gly Ile Leu Gly Leu Ala Tyr Ala Glu Ile Ala
        115                 120                 125
Arg Pro Asp Asp Ser Leu Glu Pro Phe Phe Asp Ser Leu Val Lys Gln
    130                 135                 140
Thr His Val Pro Asn Leu Phe Ser Leu Gln Leu Cys Gly Ala Gly Phe
145                 150                 155                 160
Pro Leu Asn Gln Ser Glu Val Leu Ala Ser Val Gly Gly Ser Met Ile
                165                 170                 175
Ile Gly Gly Ile Asp His Ser Leu Tyr Thr Gly Ser Leu Trp Tyr Thr
            180                 185                 190
Pro Ile Arg Arg Glu Trp Tyr Tyr Glu Val Ile Ile Val Arg Val Glu
        195                 200                 205
Ile Asn Gly Gln Asp Leu Lys Met Asp Cys Lys Glu Tyr Asn Tyr Asp
    210                 215                 220
Lys Ser Ile Val Asp Ser Gly Thr Thr Asn Leu Arg Leu Pro Lys Lys
225                 230                 235                 240
Val Phe Glu Ala Ala Val Lys Ser Ile Lys Ala Ala Ser Ser Thr Glu
                245                 250                 255
Lys Phe Pro Asp Gly Phe Trp Leu Gly Glu Gln Leu Val Cys Trp Gln
            260                 265                 270
Ala Gly Thr Thr Pro Trp Asn Ile Phe Pro Val Ile Ser Leu Tyr Leu
        275                 280                 285
Met Gly Glu Val Thr Asn Gln Ser Phe Arg Ile Thr Ile Leu Pro Gln
    290                 295                 300
Gln Tyr Leu Arg Pro Val Glu Asp Val Ala Thr Ser Gln Asp Asp Cys
305                 310                 315                 320
Tyr Lys Phe Ala Ile Ser Gln Ser Ser Thr Gly Thr Val Met Gly Ala
                325                 330                 335
Val Ile Met Glu Gly Phe Tyr Val Val Phe Asp Arg Ala Arg Lys Arg
            340                 345                 350
Ile Gly Phe Ala Val Ser Ala Cys His Val His Asp Glu Phe Arg Thr
        355                 360                 365
Ala Ala Val Glu Gly Pro Phe Val Thr Leu Asp Met Glu Asp Cys Gly
    370                 375                 380
Tyr Asn Ile Pro Gln Thr Asp Glu Ser His His His His His
385                 390                 395
```

-continued

```
<210> SEQ ID NO 6
<211> LENGTH: 32
<212> TYPE: DNA
<213> ORGANISM: Oligonucleotide Primer

<400> SEQUENCE: 6
cgctttggat ccgtggacaa cctgaggggc aa                              32

<210> SEQ ID NO 7
<211> LENGTH: 40
<212> TYPE: DNA
<213> ORGANISM: Oligonucleotide Primer

<400> SEQUENCE: 7
cgctttggta ccctatgact catctgtctg tggaatgttg                      40
```